(12) United States Patent
Lyngstadaas et al.

(10) Patent No.: US 8,029,769 B2
(45) Date of Patent: Oct. 4, 2011

(54) PROTEIN FORMULATION

(75) Inventors: S. Petter Lyngstadaas, Nesoddtangen (NO); Aaldert Molenberg, Binningen (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 12/210,350

(22) Filed: Sep. 15, 2008

(65) Prior Publication Data

US 2009/0060999 A1 Mar. 5, 2009

Related U.S. Application Data

(63) Continuation of application No. 11/721,192, filed on Oct. 24, 2007.

(60) Provisional application No. 60/636,686, filed on Dec. 16, 2004.

(30) Foreign Application Priority Data

Dec. 10, 2004 (SE) ...................................... 0403014

(51) Int. Cl.
 A61Q 11/00 (2006.01)
 A61K 38/00 (2006.01)
(52) U.S. Cl. .......................................... 424/49; 514/12
(58) Field of Classification Search ........................ None
 See application file for complete search history.

(56) References Cited

U.S. PATENT DOCUMENTS

| 4,672,032 A | 6/1987 | Slavkin et al. |
| 5,874,500 A | 2/1999 | Rhee et al. |
| 5,997,301 A | 12/1999 | Linden |
| 6,503,539 B2 | 1/2003 | Gestrelius et al. |
| 2003/0166833 A1 | 9/2003 | Lutolf et al. |
| 2003/0187232 A1 | 10/2003 | Hubbell et al. |

FOREIGN PATENT DOCUMENTS

| EP | 0337967 A2 | 10/1989 |
| EP | 0 263 086 B1 | 12/1991 |
| EP | 1 059 934 A1 | 12/2000 |
| EP | 1 153 610 A1 | 11/2001 |
| JP | 2004143165 | * 5/2004 |
| WO | WO 00/06734 | 2/2000 |
| WO | WO 00/44808 A1 | 8/2000 |
| WO | WO 00/53196 A1 | 9/2000 |
| WO | WO 01/92584 | 12/2001 |
| WO | WO 01/97834 A1 | 12/2001 |
| WO | WO 02/080994 A1 | 10/2002 |
| WO | WO 03/052901 A1 | 6/2003 |
| WO | WO 03/080144 A1 | 10/2003 |

OTHER PUBLICATIONS

Habelitz et al. "Amelogenin Induces Biomineralization at Specific pH", Materials Research Society Symposium Proceedings, 2003, vol. 774, pp. O7.8.1-O7-8-6.*
Gestrelius, et al., "Emdogain—peridontal regeneration based on biomimicry", Clin Oral Invest, vol. 4, pp. 120-125, Springer-Verlag, 2000.

International Search Report from priority application PCT/IB2005/004134.
Besson, et al., "Synthetic Peptide Substrates for a Conductimetric Assay of *Pseudomonas aeruginosa* Elastase", Analytical Biochemistry, vol. 237, No. 232, pp. 216-223, Academic Press, Inc., 1996.
Coombs, et al., "Directing Sequence-specific Proteolysis to New Targets", The Journal of Biological Chemistry, Vo. 273, No. 8, pp. 4323-4328, The American Society for Biochemistry and Molecular Biology, Inc., 1998.
Gestrelius et al. 1997; Formulation oof enamel matrix derivative for surface coating; kinetics and cell colonization. J. Clin. Periodontal (23(9 pt 2): 678-684.
Hammarström, et al., "Enamel matrix, cementum developement and regeneration", J of Clin Periodontol, vol. 24, pp. 658-668, J. Clin Periodontol, 1997.
Hata, et al., "Binding of Lipoprotein Lipase to Heparin", The Journal of Biological Chemistry, vol. 268, No. 12, pp. 8447-8457, 1993.
Harding et al., Matrix proteins-the innovative therapy changing the future for hard-to-heal wounds, Full report from the Satellite Symposium at WUWS meeting in Paris, Jul. 2004.
Haugen et al., "Central and Peripheral Neurite Outgrowth Differs in Preference for Heparin-Binding versus Integrin-Binding Sequences", The Journal of Neuroscience, vol. 12, No. 6, pp. 2034-2042, Soceity for Neuroscience, 1992.
Hern, et al., "Incorporation of adhesion peptides into nonadhesive hydrogels useful for tissue resurfacing", J Biomed Mater Res, vol. 39, pp. 266-276, John Wiley & Sons, Inc., 1998.
Kallapur, et al., "The Neural Cell Adhesion Molecule (NCAM) Heparin Binding Domain Binds to Cell Surface Heparan Sulfate Proteoglycans", Journal of Neuroscience Research, vol. 33, pp. 538-548, Wiley-Liss, Inc., 1992.
Lyngstadaas, et al., "Autocrine growth factors in human peridontal ligament cells cultured on enamel matrix derivative", J Clin Periodontol, vol. 28, pp. 181-188, J. Clin Periodontol, 2001.
Netzel-Arnett, et al., "Sequence Specificities of Human Fibroblast and Neutrophil Collagenases", The Journal of Biological Chemistry, vol. 266, No. 11, pp. 6747-6755, The American Society for Biochemistry and Molecular Biology, Inc., 1991.

(Continued)

*Primary Examiner* — Suzanne M. Noakes
(74) *Attorney, Agent, or Firm* — Rissman Hendricks & Oliverio LLP

(57) ABSTRACT

A low-concentration formulation of an active enamel substance, such as an enamel matrix, enamel matrix derivative and/or an enamel matrix protein, is intended to be used as a therapeutic, as a prophylactic and/or as a cosmetic agent. The active enamel substance is incorporated into a polymeric matrix, which is either suitable for cellular in-growth, or is cell-occlusive, so that it is released by degradation of the polymeric matrix, by enzymatic action and/or by diffusion. A new pharmaceutical and/or cosmetic formulation of an active enamel substance is provided at a lower total concentration within the formulation, wherein a spatial and/or selective regulation of release of said active enamel substance permits a greater percentage of the active enamel substance to be released at the time of appropriate cellular activity.

10 Claims, 13 Drawing Sheets

OTHER PUBLICATIONS

Schense, et al., "Cross-Linking Exogenous Bifunctional Peptides into Fibrin Gels with Factor XIIIa", Bioconjugate Chem., vol. 10, pp. 75-81, American Chemical Society, 1999.

Sierra, David H., "Fibrin Sealant Adhesive Systems: A Review of Their Chemistry, Material Properties and Clinical Applications", Journal of Biomaterials Applications, vol. 7, pp. 309-352, Technomic Publishing Co., Inc., 1993.

Smith, et al., "Rapid Identification of Highly Active and Selective Substrates for Stromelysin and Matrilysin Using Bacteriophage Peptide Display Libraries", The Journal of Biological Chemistry, vol. 270, No. 12, pp. 6440-6449, The American Society for Biochemistry and Molecular Biology, Inc., 1995.

Takagi, et al., "Amino Acid Sequence Studies on the α Chain of Human Fibrinogen. Location of Four Plasmin Attack Points and a Covalent Cross-Linking Site", Biochemistry, vol. 14, No. 23, pp. 5149-5156, 1975.

Ten Cate, "Oral Histology Development, Structure and Function", Eur J Oral Science, vol. 106, pp. 282-291, 1994.

Tyler-Cross, et al., "Heparin binding domain peptides of antithrombin III: Analysis by isothermal titration calorimetry and circular dichroism spectroscopy", Protein Science, vol. 3, pp. 620-627, The Protein Society, 1994.

Williams, et al., "Exogenous Matrix Precursors Promote Functional Nerve Regeneration Across a 15-mm Gap Within a Silicone Chamber in the Rat", The Journal of Comparative Neurology, vol. 264, pp. 284-290, Alan R. Liss, Inc., 1987.

Zucker, et al., "Platelet Factor 4: Production, Structure, and Physiologic and Immunologic Action (43309)", Exper Biol Med, pp. 693-702, Society for Experimental Biology and Medicine, 1991.

Japanese Patent Application No. JP2004143165A to Fukae English language translation.

Christoph H.F. Hämmerle & Ronald E. Jung, "Bone augementation by means of barrier membranes", Periodontology 2000, vol. 33, 2003, 36-53.

Wang, K., et al., "Controlled Release of Enamel Matrix Protein from PEG-based Hydrogels", 81st General Session of the International Ass. for Dental Research, p. 1, xp-002630576, 2003.

Hattar, S., et al., "Potential of biomimetic surfaces to promote in vitro osteoblast-like cell differentiation", Biomaterials vol. 26, pp. 839-848, May 18, 2004.

Craemer, J., et al., "Bioengineering human tooth implants", The IADR/AADR/CADR 83rd General Session, p. 1, xp-002630577, Mar. 2005.

Search Report of EP No. 10185085.7 dated May 3, 2011.

* cited by examiner

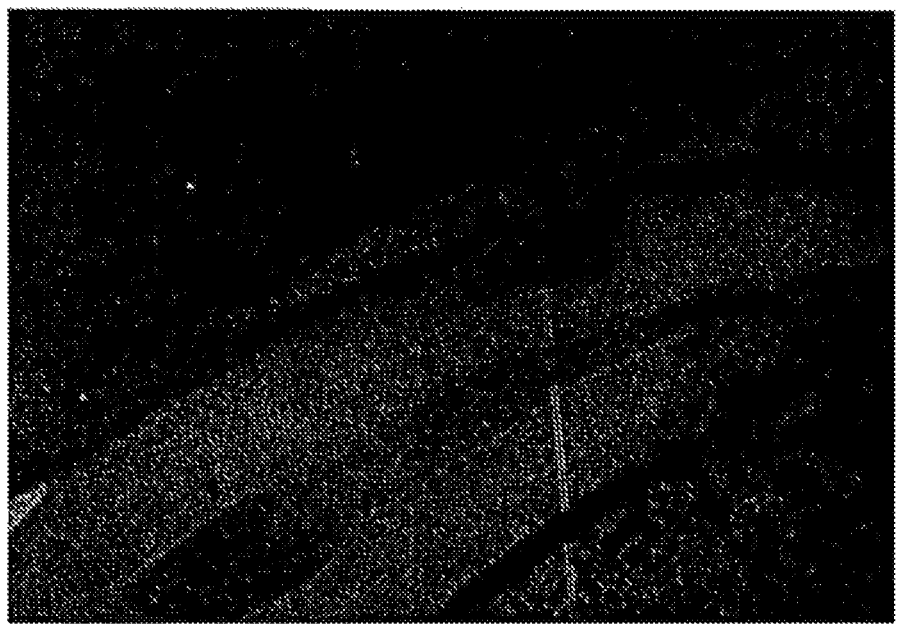
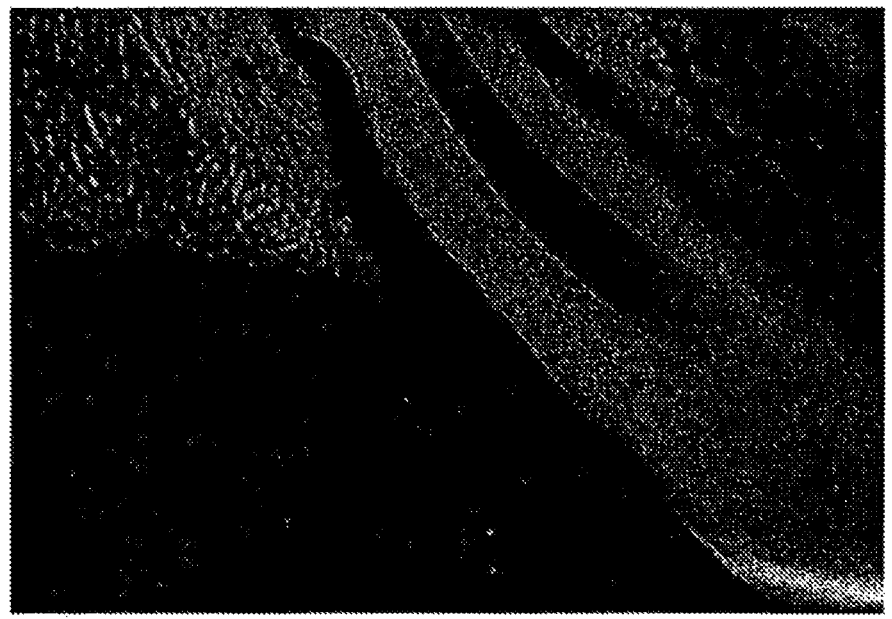
Figure 7 A/B

PROTEIN FORMULATION

This application is a continuation of and claims priority to U.S. Ser. No. 11/721,192, filed Jun. 8, 2007, which is a national stage application of and claims priority to PCT/IB05/ 04134, filed Dec. 12, 2005, which claims priority to Swedish Application No. 0403014-4, filed Dec. 10, 2004, and which also claims priority to U.S. Ser. No. 60/636,686, filed Dec. 16, 2004, the disclosures of which are incorporated herein in their entirety.

FIELD OF THE INVENTION

The present invention relates to a new and improved low-concentration formulation of an active enamel substance, such as an enamel matrix, enamel matrix derivative and/or an enamel matrix protein, intended to be used as therapeutic, as prophylactic and/or as cosmetic agent. In the present invention, said active enamel substance is incorporated into a polymeric matrix, in particular intended for use in tissue repair, regeneration and/or remodelling, for inducing binding between parts of living mineralized tissue, for bonding a piece of living mineralized tissue to a bonding site on a piece of other living tissue, for improving the healing of a wound in skin or mucosa, for preventing or treating an infection or an inflammatory condition, for the formation or regeneration of dentin, for promoting the take of a graft, for treating epithelially derived benign, semi-malignant or malignant neoplasms, for the induction of apoptosis, or for filling a wound cavity and/or tissue defect following a procedure and/or trauma, such as cytoreductive surgery.

In the present invention, the active enamel substance can be incorporated into the polymeric matrix so that it is released by degradation of the polymeric matrix, by enzymatic action and/or by diffusion. Said polymeric matrix is either suitable for cellular in-growth, or cell-occlusive.

Comprised in the invention is thus in particular a new pharmaceutical and/or cosmetic formulation of an active enamel substance at a lower total concentration within the formulation, wherein a spatial and/or selective regulation of release of said active enamel substance permits a greater percentage of the active enamel substance to be released at the time of appropriate cellular activity.

SUMMARY OF THE INVENTION

The active enamel substances of the present invention (the term "an active enamel substance" is in the present context used for an enamel matrix, an enamel matrix derivative and/or an enamel matrix protein), are able to induce not only one but an orchestrated cascade of factors, naturally found in tissues developing adjacent to the enamel matrix. They mimic the natural environment of a developing tissue and thus mimic a natural stimulation for tissue regeneration, cell differentiation and/or maturation.

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. As shown by the present inventors prior to the present invention, enamel matrix proteins can therefore promote periodontal regeneration through mimicking the natural attachment development in the tooth (Gestrelius S, Lyngstadaas S P, Hammarstrøm L. Emdogain—periodontal regeneration based on biomimicry. Clin Oral Invest 4:120-125 (2000)).

The enamel matrix is composed of a number of proteins, such as amelogenins, enamelin, tuft protein, proteases, and albumin. Amelogenins, the major constituent of the enamel matrix, are a family of hydrophobic proteins derived from a single gene by alternative splicing and controlled post secretory processing. They are highly conserved throughout vertebrate evolution and demonstrate a high overall level of sequence homology among all higher vertebrates examined (approximately 80%). In fact, the sequences of porcine and human amelogenin gene transcript differ only in 4% of the bases. Thus, enamel matrix proteins, although of porcine origin, are considered "self" when encountered in the human body and can promote dental regeneration in humans without triggering allergic responses or other undesirable reactions.

Enamel matrix derivatives (e.g. EMD), in the form of a purified acid extract of proteins from pig enamel matrix, have previously been successfully employed to restore functional periodontal ligament, cementum and alveolar bone in patients with severe tooth attachment loss (Hammarström et al., 1997, Journal of Clinical Periodontology 24, 658-668).

Furthermore, in studies on cultured periodontal ligament cells (PDL), it was shown that the attachment rate, growth and metabolism of these cells were significantly increased when EMD was present in the cultures. Also, cells exposed to EMD showed increased intracellular cAMP signalling and autocrine production of growth factors, when compared to controls. Epithelial cells on the other hand, although increasing cAMP signalling and growth factor secretion when EMD was present, were inhibited in both proliferation and growth (Lyngstadaas et al., 2001, Journal of Clinical Periodontology 28, 181-188).

Enamel matrix proteins and enamel matrix derivatives (EMD) have previously been described in the patent literature to be able to induce hard tissue formation (e.g. enamel formation, U.S. Pat. No. 4,672,032 (Slavkin)), endorse binding between hard tissues (EP-B-0 337 967 and EP-B-0 263 086), promote open wound healing, such as of skin and mucosa, have a beneficial effect on treatment of infections and inflammatory diseases (EPO 1, 1059934 and EPO II, 01201915.4), induce regeneration of dentin (WO 01/97834), promote the take of a graft (WO 00/53197), induce apoptosis in the treatment of neoplasms (WO 00/53196), and facilitate filling a wound cavity and/or tissue defect following from a procedure and/or trauma, such as a cytoreductive surgery (WO 02/080994).

For tissue repair or regeneration, as exemplified in the medical indications for EMD described above, cells must migrate into a wound bed, proliferate, differentiate, and form a final tissue shape. Multiple cell populations must often participate in this morphogenetic response.

Nonetheless, any of the above described effects or uses of active enamel substances, such as enamel matrix, enamel matrix derivatives and/or enamel matrix proteins, have been documented for formulations of active enamel substances at relatively high concentrations. A typical concentration being between 10-30 mg/ml. No effect has so far been able to be observed with formulations of active enamel substances at lower concentrations. Without wishing to limit the present invention to a specific theory, this is potentially be due to the fact that all pharmaceutical and/or cosmetic formulations employed so far have been designed to release the active enamel substance in an uncontrolled manner.

In analogy, to be able to lower the dosage of administered basic fibroblast growth factor, controlled delivery devices were designed based on the use of immobilized heparin to sequester the growth factor. For example, Edelman et al. (Biomaterials 1991 September; 12(7):619-26) used heparin-conjugated SEPHAROSE™ beads within alginate. The beads served as reservoirs that released basic fibroblast growth factor ("bFGF") slowly based on the binding and dissociation of bFGF with heparin.

It has also been demonstrated that bi-domain peptides, which contain a factor XIIIa substrate sequence and a bioactive peptide sequence, can be cross-linked into fibrin gels and that the bioactive peptide retains its cellular activity in vitro (Schense, J. C., et al. (1999) *Bioconj. Chem.* 10:75-81).

Furthermore, in (US 2003/0187232 and US 2003/0166833), the incorporating of entire growth factor proteins into protein or polysaccharide matrices was shown based on binding heparin to a matrix by either covalent or non-covalent methods, to form a heparin-matrix. The heparin then non-covalently bound heparin-binding growth factors to the protein matrix. Also, a fusion protein was shown containing a crosslinking region such as a factor XIIIa substrate and the native protein sequence. Incorporation of degradable linkages between the matrix and the bioactive factors were postulated to be particularly useful for long-term drug delivery.

The present application relates to the beneficial effects of a new and improved formulation of active enamel substances, applicable in all the above mentioned medical, therapeutic and cosmetic uses, wherein said active enamel substance is incorporated into a protein matrix, synthetic matrix and/or polysaccharide matrix, analogous to matrices shown in US 2003/0187232 and US 2003/0166833, including combinations of two or more of the foregoing matrices, so that the active enamel substance is released by degradation of the matrix and/or by enzymatic action and/or diffusion, thus effectively lowering the necessary total dose within the formulation and facilitating a spatial regulation of release, which permits a greater percentage of the active enamel substance to be released at the appropriate time of cellular activity.

The present invention for the first time discloses a low-concentration pharmaceutical, therapeutic and/or cosmetic formulation for administering an active enamel substance, comprising a polymeric matrix, which can be suitable for cellular growth or in-growth, or be cell-occlusive, and at least one active enamel substance, wherein the concentration of said active enamel substance in the formulation is no more than 5 mg/ml, such as about 5 mg, or less than 5 mg/ml, such as less than 4.9 mg/ml, 4.5 mg/ml, 4 mg/ml, 3.5 mg/ml, 3 mg/ml, 2.5 mg/ml, 2 mg/ml, 1.5 mg/ml, 1 mg/ml, 750 µg/ml, 500 µg/ml, 250 µg/ml, 150 µg/ml, 100 µg/ml, 50 µg/ml, 25 µg/ml, 20 µg/ml, 10 µg/ml, 5 µg/ml, or 1 µg/ml.

The present invention provides products and methods for hard and soft tissue repair, regeneration, or remodelling, in particular for bone and tooth growth, using natural and/or synthetic polymeric matrices having an active enamel substance releasably incorporated or enclosed therein. The polymeric matrices are biocompatible and/or biodegradable. They can be formed in vitro or in vivo at the time of implantation. A typical polymeric matrix is either suitable for cellular growth or in-growth, or cell-occlusive, depending on the size of the pores of the matrix. The active enamel substance can be incorporated, attached and/or enclosed into the polymeric matrices, still retaining its full bioactivity. What is more, the active enamel substance can be releasably incorporated, attached and/or enclosed using techniques that provide control over the time-point of release and/or the degree the active enamel substance is released at. Such a formulation can e.g. be used directly or indirectly for tissue repair, using the polymeric matrix as a controlled release vehicle.

Formulations comprising active enamel substances described prior to the present invention are most commonly administered at substantially higher concentrations than the concentrations envisioned herein, such as at least 30 mg/ml concentration of said active enamel substance. What is more, formulation comprising below 5 mg protein/ml have actually been established in the field to be insufficient, as is documented in example 1 for EMD, which is formulated in a conventional PGA gel.

As documented convincingly in the examples, the inventors were surprisingly able to demonstrate that the new low-concentration formulation, which comprises a polymeric matrix and an active enamel substance, allows a lowering of the necessary concentration of the active enamel substance to between 1 µg/ml and 5 mg/ml, such as between 100 µg/ml and 500 µg/ml, 50 µg/ml and 250 µg/ml, 50 µg/ml and 150 µg/ml, 10 µg/ml and 200 µg/ml, 10 µg/ml and 100 µg/ml, 5 µg/ml and 100 µg/ml, 1 µg/ml and 50 µg/ml, or even less.

The polymeric matrix related to in the present invention is formed by crosslinking precursor molecules to a polymeric network ionically, covalently, or by combinations thereof, or by swelling of one or more polymeric material(s), or by physical crosslinks, e.g. by crosslinking points formed through aggregation of endblocks through phase or solubility differences. In a first embodiment of the present invention, said matrix forms a polymeric network having sufficient inter-polymer spacing to allow for growth, in-growth and/or migration of cells into the matrix. Typically, in this particular embodiment, the crosslinked polymeric matrix forms a gel. In a second embodiment of the present invention, said matrix forms a polymeric network with a narrow pore size, which occludes in-growth and/or migration of cells into the matrix and which is sufficiently narrow to restrict the active enamel substance inside the matrix. Additionally, in another embodiment still, said second embodiment can over time be degraded to contain sufficient inter-polymer spacing to allow for growth, in-growth and/or migration of cells into the matrix.

The above described two specific embodiments of the present invention serve different and specific purposes, and are thus alternatively preferable, depending on the intended use of the low-concentration formulation of active enamel substances. For example, a cell-occlusive matrix form can be preferred when the intention of use is to provide a biodegradable barrier which prevents surrounding soft tissue from interaction with the region to be protected, which will e.g. prevent infection of a wound. In another example, this form is especially preferred when a barrier function is sought for during complete healing time for effective bone regeneration, such as in an implant bed defect. Such an embodiment can take the form of a membrane. Additionally, such a preferred matrix can be designed to e.g. include predestined sites for enzymatic or hydrolytic degradation, and thus in time become cell invasive. On the other hand, if e.g. a soft tissue wound or a wound cavity, resulting from cytoreductive surgery, is to be filled with a low-concentration formulation comprising an active enamel substance, cellular in-growth and/or migration is beneficial for the healing of said wound, and thus typically a gel formulation is preferred that has a pore size that is sufficiently large to allow cellular in-growth and/or migration. Again, typical PEG gels do not always start out with pore sizes that are sufficiently large to allow cellular in-growth and/or migration, but can be designed in time, e.g. after enzymatical degradation by enzymes released by invading or adjacent cells, or by hydrolytical or mechanical degradation to contain pore sizes sufficiently large to allow cellular in-growth and/or migration. Also, in some applications, said two specific forms might be interchangeable, or used together.

In one embodiment, the polymeric matrix is formed of proteins, preferably proteins naturally present in the patient, into which the polymeric matrix is to be implanted. A particularly preferred natural polymeric matrix protein is fibrin, although polymeric matrices made from other proteins, such as collagen and gelatin can also be used. Polysaccharides and glycoproteins may also be used to form the polymeric matrix.

In another, equally preferred embodiment, synthetic polymers are employed to form the polymeric matrix, which are crosslinked by ionic or covalent or physical binding.

The polymeric matrix material is preferably biodegradable by naturally present enzymes or by hydrolysis. The rate of degradation can furthermore be manipulated by the degree of crosslinking and the inclusion of protease inhibitors in the polymeric matrix. The degradable sites allow for more specific release of the active enamel substance from matrices. For example, degradation based on enzymatic activity allows for the release of an active enamel substance to be controlled by a cellular process, such as localized proteolysis, rather than by diffusion of the active enamel substance through the gel. The degradable site or linkage is cleaved by enzymes released from cells which invade the polymeric matrix or which surround it. This allows active enamel substances to be released at different rates within the same material, depending on the location of cells within/adjacent to the material.

Cell specific proteolytic activity is e.g. vital in those applications, which occur over long periods of time. A controlled release of the active enamel substance as described herein, effectively reduces the amount of total active enamel substance needed, since its release is controlled by cellular processes. Conservation of active enamel substance and its bioavailability are distinct advantages of exploiting cell specific proteolytic activity over the use of diffusion controlled release devices which characteristically result in the loss of a significant amount of active enamel substance in an initial burst release.

FIGURES

Figure 8:
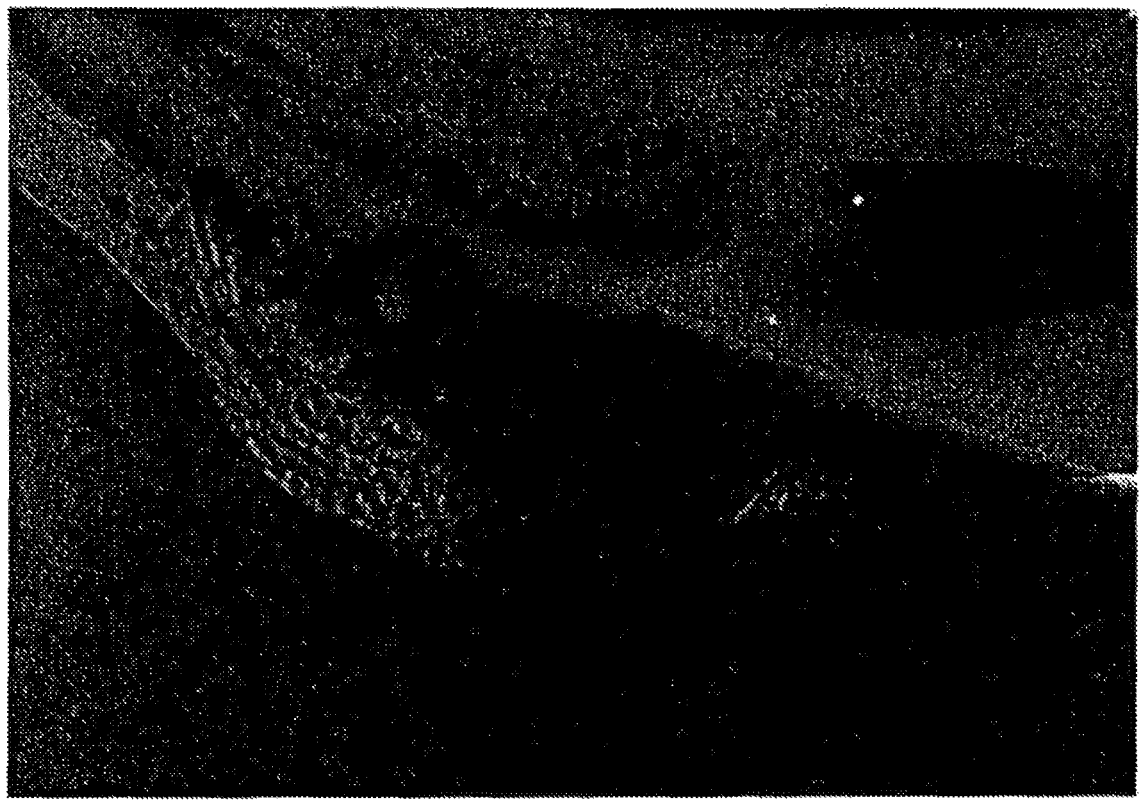
Figure 9:
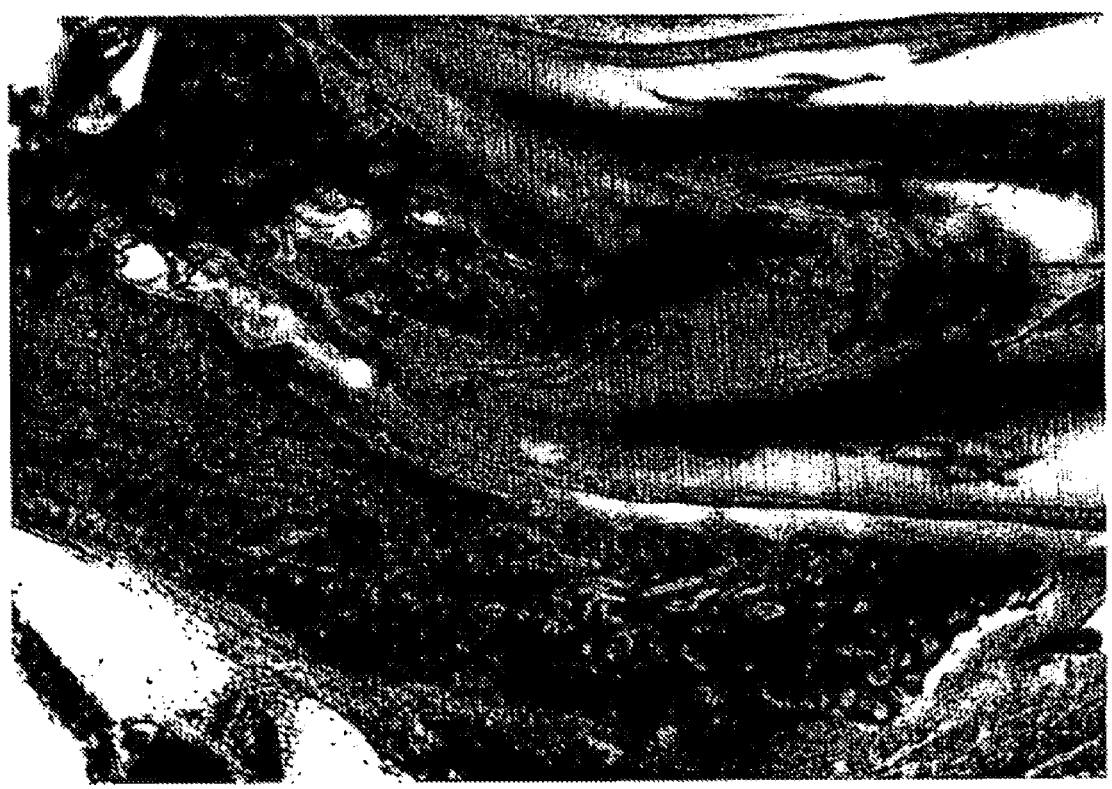
Figure 10:
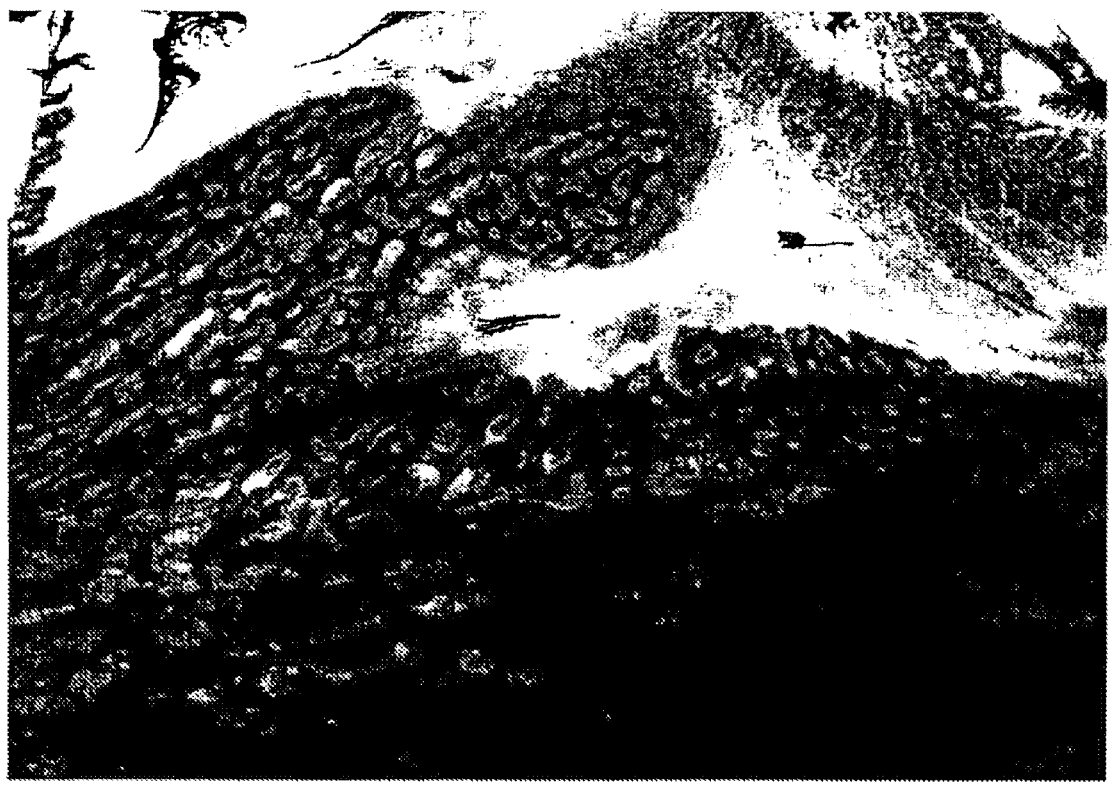
Figure 11:
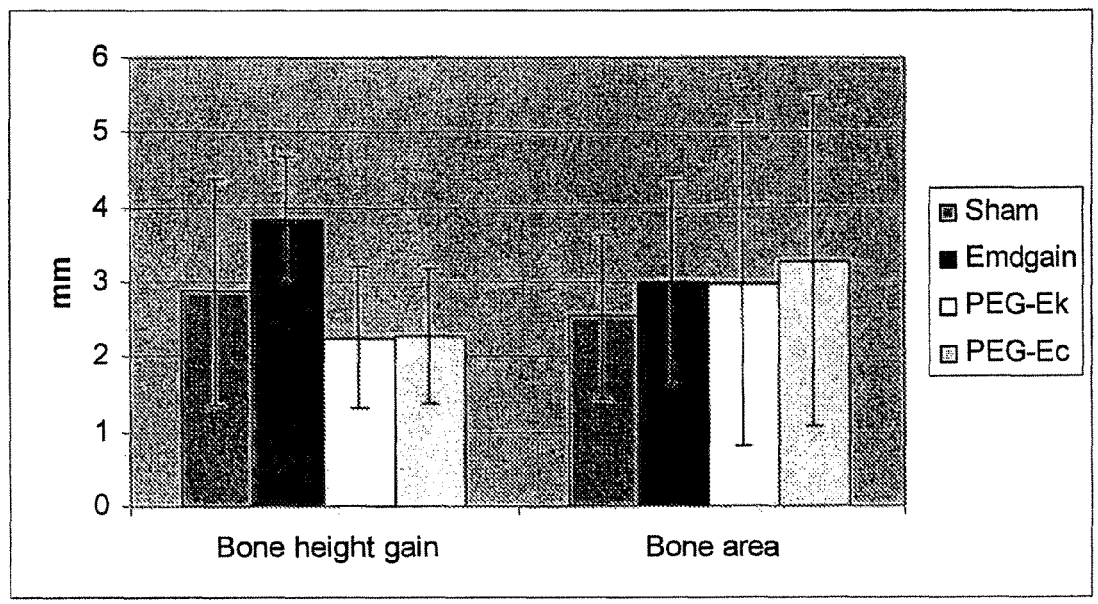
Figure 12:
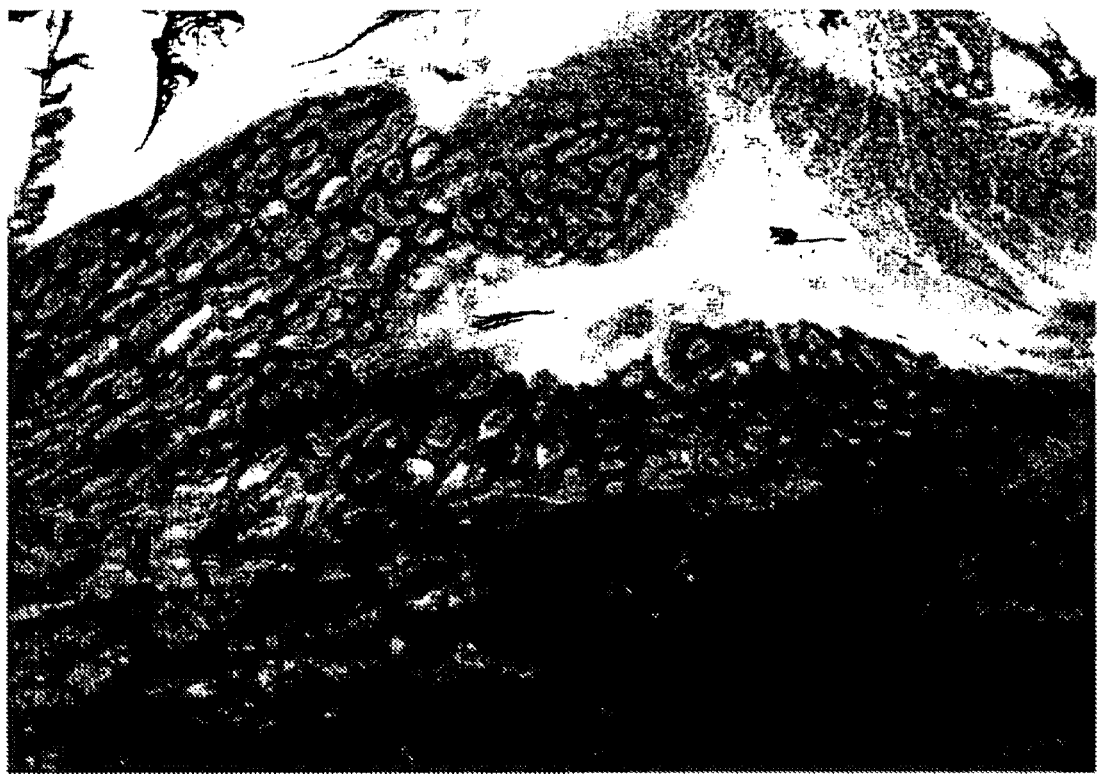
Figure 13:
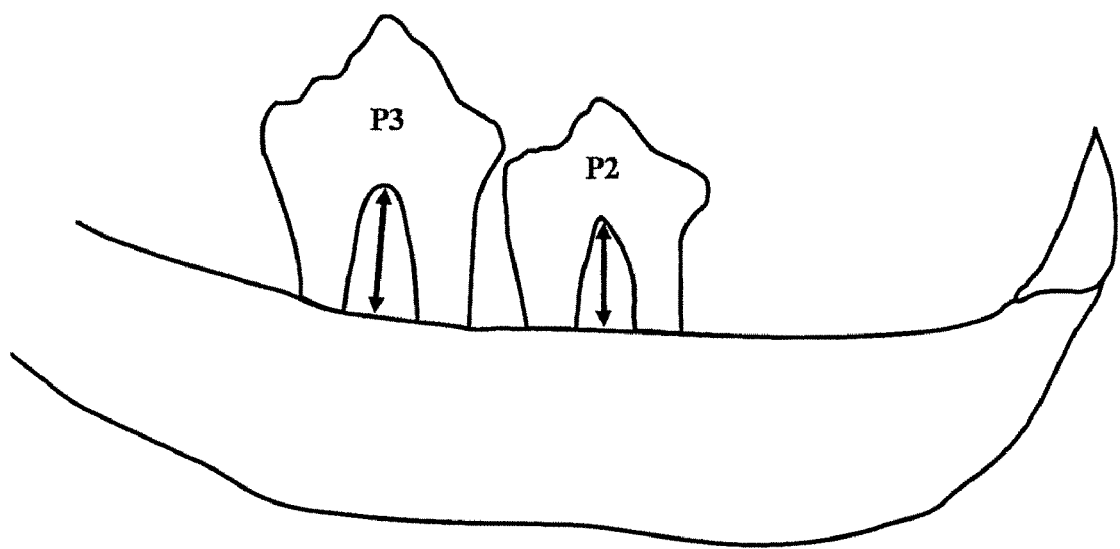

FIG. 7 histologically documents the regeneration of a mature and lamellar bone separated from the new cement by a well organized periodontal ligament. 7A Emdogain, 7B PEG/Ec;

FIG. 8 histologically documents the regeneration of a mature and lamellar bone PEG/Ec;

FIG. 9 histologically shows the presence of the periodontal ligament after treatment with PEG-Ec (CMC);

FIG. 10 histologically shows the presence of the periodontal ligament after treatment with PEG-Ec (CMC);

FIG. 11 shows the quantitative measurement of bone regain from microXrays, where Emdogain® reached the highest performance (about 4 mm) with a statistical significance comparatively to PEG-Ec or PEG-Ek (p<0.005);

FIG. 12 histologically documents the morphologies of the regenerated bone structures, which were different between the two types of the PEG-Ec or PEG-Ek and Emdogain®; and FIG. 13 shows a surgical set-up for the treatment of class 3 furcation defects in dogs; in the figure, each arrow corresponds to approximately 5 mm.

DETAILED DISCLOSURE

Active Enamel Substances

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is e.g. fish skin. In the present context, the term "an active enamel substance" is used to encompass enamel matrix, enamel matrix derivatives and/or enamel matrix proteins nondiscriminant of their source.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, alternatively followed by freeze-drying. Enzymes may alternatively be deactivated by treatment with heat or solvents, in which case the derivatives may be stored in liquid form without freeze-drying.

As an alternative source of the enamel matrix derivatives or proteins one may also use generally applicable synthetic routes, well known to a person skilled in the art, or use cultivated eukaryotic and/or prokaryotic cells modified by DNA-techniques. The enamel matrix proteins may thus be of recombinant and/or synthetic origin (see, e.g., Sambrook, J. et al.: Molecular Cloning, Cold Spring Harbor Laboratory Press, 1989).

Thus, one aspect of the present invention relates to a pharmaceutical and/or therapeutic formulation for administering an active enamel substance, comprising a polymeric matrix and at least one recombinant or synthetic protein selected from the group of active enamel substances, which can be chemically modified. In a preferred embodiment, said protein has at least one cysteine residue which is situated in the N-terminus, or the C-terminus of said protein.

In the present context, enamel matrix derivatives are derivatives of enamel matrix which include one or several enamel matrix proteins or parts or fragments of such proteins, produced naturally by alternate splicing or processing, or by either enzymatic or chemical cleavage of a natural length protein, or by synthesis of polypeptides in vitro or in vivo (e.g. recombinant DNA methods and/or cultivation of diploid cells). Enamel matrix protein derivatives also include enamel matrix related polypeptides or proteins. The polypeptides or proteins may be bound to a suitable biodegradable carrier molecule, such as polyamine acids or polysaccharides, or combinations thereof. Furthermore, the term enamel matrix derivatives also encompass synthetic analogous substances.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides or oligopeptides.

Enamel matrix proteins are proteins that normally are present in enamel matrix, i.e. the precursor for enamel (Ten Cate: Oral Histology, 1994; Robinson: Eur. J. Oral Science, January 1998, 106 Suppl. 1:282-91), or proteins, peptides or fragments of such proteins which can be obtained by cleavage of such proteins. In general, such proteins have a molecular weight below 120,000 Dalton and include amelogenins, non-amelogenins, proline-rich non-amelogenins and tuftelins.

Examples of proteins for use according to the invention are amelogenins, proline-rich non-amelogenins, tuftelin, tuft proteins, serum proteins, salivary proteins, ameloblastin, sheathlin, fragments and derivatives thereof, and mixtures thereof. A preparation containing an active enamel substance for use according to the invention may also contain at least two of the aforementioned proteinaceous substances. Moreover, other proteins for use according to the invention are found in the marketed product EMDOGAIN® (BIORA AB, Sweden).

EMDOGAIN® (BIORA AB, S-205 12 Malmö, Sweden), an enamel matrix derivative well known in the art, contains 30 mg Enamel Matrix protein, heated for 3 hours at about 80° C. in order to inactivate residual proteases, per 1 ml Vehicle Solution (Propylene Glycol Alginate), which are mixed prior to application, unless the protein and the Vehicle are tested separately. The weight ratio is about 80/8/12 between the main protein peaks at 20, 14 and 5 kDa, respectively.

In general, the major proteins of an enamel matrix are known as amelogenins. They constitute about 90% w/w of the matrix proteins. The remaining 10% w/w includes proline-rich non-amelogenins, tuftelin, tuft proteins, serum proteins and at least one salivary protein; however, other proteins may also be present such as, e.g., amelin (ameloblastin, sheathlin) which have been identified in association with enamel matrix. Furthermore, the various proteins may be synthesised and/or processed in several different sizes (i.e. different molecular weights). Thus, the dominating proteins in enamel matrix, amelogenins, have been found to exist in several different sizes that together form supramolecular aggregates. They are markedly hydrophobic substances that under physiologically conditions form aggregates. They may carry or be carriers for other proteins or peptides. The size of the aggregates is variable, comprising an average of size between about 10 nm and 100 µm, 100 nm-10 µm, or 50 nm-1 µm, often bigger, such as between 100 nm-100 µm, 20 nm-100 µm, 25 nm-100 µm, 50 nm-100 µm, 10-100 nm, 10-25 nm, 100-50 nm, 20-30 nm, 20-50 nm, 20-60 nm, 25-45 nm, 25 nm-50 nm, 25 nm-75 nm, 50 nm-75 nm, etc. In general, the size of the aggregates can be variable, depending also on the concentration of proteins, peptides and/or fragments in a given solution/matrix and the presence of other substances in the matrix.

A presently preferred embodiment of the invention therefore relates to a pharmaceutical, cosmetic and/or therapeutic formulation comprising an amelogenin, and/or at least a fragment and/or a subfragment of an amelogenin.

Another, equally preferred embodiment further relates to a pharmaceutical and/or therapeutic formulation comprising a pre-pro amelogenin.

Other protein/polypeptide substances are also contemplated to be suitable for use according to the present invention. Examples include proteins or fragments of proteins such as proline-rich proteins and polyproline.

Other examples of substances that are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size, ranging from the size of proteins to that of short peptides.

Proteins, polypeptides, peptides and/or subfragments thereof, related to in this invention. may be in a substantially isolated or purified form. It will be understood that the proteins, polypeptides, peptides and/or subfragments thereof may be mixed with carriers or diluents, which will not interfere with the intended purpose of the proteins, polypeptides, peptides and/or subfragments thereof and which will still be regarded as substantially isolated. Such a substantially purified form will generally comprise the protein, peptide and/or a fragment thereof in a preparation in which more than 90%, e.g. 95%, 96%, 97%, 98% or 99% of the protein in the preparation is a protein, polypeptide, peptide and/or fragment of the invention.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a protein, polypeptide, peptide and/or subfragment of an active enamel substance according to the invention, is also considered to be inside the scope of the present invention.

By a protein, polypeptide, peptide and/or fragment thereof having an amino acid sequence at least, for example 95% identical to a reference amino acid sequence, is intended that the amino acid sequence of e.g. the polypeptide is identical to the reference sequence, except that the amino acid sequence may include up to 5 point mutations per each 100 amino acids of the reference amino acid sequence. In other words, to obtain a polypeptide having an amino acid sequence at least 950% identical to a reference amino acid sequence: up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

The low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenins, tuftelin, etc. with molecular weights (as measured in vitro with SDS-PAGE) below about 60,000 Dalton but proteins having a molecular weight above 60,000 Dalton have also promising properties as candidates for e.g. promoting connective tissue growth.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS PAGE electrophoresis.

A preparation of an active enamel substance for use according to the Invention may also contain a mixture of active enamel substances with different molecular weights.

Accordingly, it is contemplated that the active enamel substance for use according to the invention has a molecular weight of up to about 40,000 such as, e.g. a molecular weight of between about 5,000 and about 25,000.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as tuftelin or proteolytic enzymes normally found in enamel matrix can be added and carried by the amelogenin aggregate.

In general, the enamel matrix, enamel matrix derivatives and enamel matrix proteins are hydrophobic substances, i.e. less soluble in water, especially at increased temperatures. Typically, these proteins are soluble at non-physiological pH values and at a low temperature such as about 4-20° C., while they will aggregate and precipitate at body temperature (35-37° C.) and neutral pH.

In a specifically preferred embodiment, a low-concentration formulation of active enamel substances for use according to the present invention, thus comprises active enamel substances which at least partially are aggregated, and/or which after application in vivo are capable of forming aggregates. The particle size of said aggregates being in a range of from about 200 μm to about 10 nm, such as between 100 μm and 10 nm, 10 μm and 100 nm, 1 μm and 20 nm, 1 μm and 10 nm, 5 μm and 10 nm, 10 μm and 1 nm, 100 μm and 10 nm, 100 μm and 1 nm, 1 μm and 1 nm, 1 μm and 5 nm, 1 μm and 15 nm.

As the polymeric matrix related to in the present invention is formed by crosslinking precursor molecules to a polymeric network, said matrix can form a polymeric network having sufficiently narrow inter-polymer spacing to allow confinement of aggregates of active enamel substances inside the matrix. In a presently preferred embodiment, such a polymeric network with sufficiently narrow pore sizes will be formed at a neutral pH, and/or in situ after application of the precursor molecules in the patient's body, thus automatically bringing on the aggregation and/or precipitation of the active enamel substances.

In accordance to the present invention, an active enamel substance may be used together with other active drug substances such as, e.g. anti-bacterial, anti-inflammatory, antiviral, antifungal substances or in combination with local chemotherapy, inducers of apoptosis, growth factors such as, e.g., TGFβ, PDGF, IGF, FGF, EGF, keratinocyte growth factor or peptide analogues thereof. Enzymes—either inherently present in the enamel matrix or preparation thereof, or added—may also be used in combination with an enamel matrix, enamel matrix derivative and/or enamel matrix protein, especially proteases.

Depending on the use of the active enamel substance, a composition may be a pharmaceutical and/or therapeutic, or a cosmetic composition. In the following the term "pharmaceutical and/or therapeutic composition" is also intended to embrace cosmetic compositions as well as compositions belonging to the so-called grey area between pharmaceuticals and cosmetics, namely cosmeceuticals.

A pharmaceutical and/or therapeutic composition comprising an active enamel substance serves as a drug delivery system. In the present context the term "drug delivery system" denotes a pharmaceutical and/or therapeutic composition (a pharmaceutical and/or therapeutic formulation or a dosage form) that upon administration presents the active substance to the body of a human or an animal.

Apart from the active enamel substance and the polymeric matrix, a pharmaceutical and/or therapeutic composition for use according to the invention may of course also comprise further pharmaceutically or cosmetically acceptable excipients.

A pharmaceutically or cosmetically acceptable excipient is presently defined as a substance that is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical and/or therapeutic formulation can find guidance in e.g., "Remington's Pharmaceutical Sciences", 18th Edition, Mack Publishing Company, Easton, 1990.

Fibrin Matrices

Fibrin is a natural material which has been reported for several biomedical applications. Fibrin has been described as material for cell ingrowth matrices in U.S. Pat. No. 6,331,422 to Hubbell et al. Fibrin gels have prior been used as sealants because of their ability to bind to many tissues and their natural role in wound healing. Some specific applications include use as a sealant for vascular graft attachment, heart valve attachment, bone positioning in fractures and tendon repair (Sierra, D. H., Journal of Biomaterials Applications, 7:309-352 (1993)). Additionally, these gels have been used as drug delivery devices, and for neuronal regeneration (Williams, et al., Journal of Comparative Neurobiology, 264:284-290 (1987)).

The process by which fibrinogen is polymerized into fibrin has also been characterized. Initially, a protease cleaves the dimeric fibrinogen molecule at the two symmetric sites. There are several possible proteases than can cleave fibrinogen, including thrombin, reptilase, and protease III, and each one severs the protein at a different site (Francis, et al., Blood Cells, 19:291-307, 1993). Once the fibrinogen is cleaved, a self-polymerization step occurs in which the fibrinogen monomers come together and form a non-covalently crosslinked polymer gel (Sierra, 1993). This self-assembly happens because binding sites become exposed after protease cleavage occurs. Once they are exposed, these binding sites in the center of the molecule can bind to other sites on the fibrinogen chains, which are present at the ends of the peptide chains (Stryer, L. In Biochemistry, W. H. Freeman & Company, NY, 1975). In this manner, a polymer network is formed. Factor XIIIa, a transglutaminase activated from Factor XIII by thrombin proteolysis, may then covalently crosslink the polymer network. Other transglutaminases exist and may also be involved in covalent crosslinking and grafting to the fibrin network.

Once a crosslinked fibrin gel is formed, the subsequent degradation is tightly controlled. One of the key molecules in controlling the degradation of fibrin is α2-plasmin inhibitor (Aoki, N., Progress in Cardiovascular Disease, 21:267-286, 1979). This molecule acts by crosslinking to the α chain of fibrin through the action of Factor XIIIa (Sakata, et al., Journal of Clinical Investigation, 65:290-297, 1980). By attaching itself to the gel, a high concentration of inhibitor can be localized to the gel. The inhibitor then acts by preventing the binding of plasminogen to fibrin (Aoki, et al., Thrombosis and Haemostasis, 39:22-31, 1978) and inactivating plasmin (Aoki, 1979). The α2-plasmin inhibitor contains a glutamine substrate. The exact sequence has been identified as NQEQVSPL (SEQ ID NO: 12), with the first glutamine being the active amino acid for crosslinking.

It has been demonstrated that bi-domain peptides, which contain a factor XIIIa substrate sequence and a bioactive peptide sequence, can be cross-linked into fibrin gels and that this bioactive peptide retains its cellular activity in vitro (Schense, J. C., et al. (1999) Bioconj. Chem. 10:75-81).

A preferred pharmaceutical and/or therapeutic formulation of the present invention thus comprises a polymeric matrix, which is suitable for cellular growth or in-growth, or is cell-occlusive, and at least one protein selected from the group of active enamel substances, wherein the concentration of said active enamel substance is no more than 5 mg/ml formulation, and wherein the polymeric matrix comprises fibrin. In said pharmaceutical and/or therapeutic formulation, an active enamel substance according to the present invention can be coupled to a transglutaminase substrate domain, such as a factor XIIIa substrate sequence.

This Factor XIIIa substrate sequence may e.g. include GAKDV, KKKK, or NQEQVSPL. The coupling between the active enamel substance and the transglutaminase substrate domain can be performed by chemical synthesis.

Alternatively, the transglutaminase substrate domain can be a substrate for a transglutaminase other than Factor XIIIa. The most preferred Factor XIIIa substrate domain has an amino acid sequence of NQEQVSPL, but also other proteins that transglutaminase recognizes, such as fibronectin, could be coupled to the transglutaminase substrate peptide.

TABLE 1

Transglutaminase substrate domains

| | |
|---|---|
| YRGDTIGEGQQHHLGG | A peptide with glutamine at the transglutaminase coupling site in the chain of fibrinogen |
| GAKDV | A peptide that mimics the lysine coupling site in the chain of fibrinogen |

TABLE 1-continued

Transglutaminase substrate domains

| | |
|---|---|
| KKKK | A peptide with a polylysine at a random coupling site |
| NQEQVSPL | A peptide that mimics the crosslinking site in α2-plasmin inhibitor (abbreviated TG) |

Synthetic Matrices

Crosslinking reactions for forming synthetic matrices for application in the body include (i) free-radical polymerization between two or more precursors containing unsaturated double bonds, as described in Hem et al., J. Biomed. Mater. Res. 39:266-276 (1998), (ii) nucleophilic substitution reaction such as e.g. between a precursor including an amine group and a precursor including a succinimidyl group as disclosed in U.S. Pat. No. 5,874,500 to Rhee et al., (iii) condensation and addition reactions and (iv) Michael type addition reaction between a strong nucleophile and a conjugated unsaturated group or bond (as a strong electrophile). Particularly preferred is the reaction between a precursor molecule having a thiol or amine group as the nucleophilic group and precursor molecules including acrylate or vinyl sulfone groups as electrophilic groups. Most preferred as the nucleophilic group is the thiol group. Michael type addition reactions are described in WO 00/44808 (Hubbell et al.). Michael type addition reactions allow for in situ crosslinking of at least a first and a second precursor component under physiological conditions in a self-selective manner, even in the presence of sensitive biological materials. When one of the precursor components has a functionality of at least two, and at least one of the other precursor components has a functionality greater than two, the system will self-selectively react to form a cross-linked three dimensional biomaterial.

Consequently, one aspect of the present invention relates to a pharmaceutical and/or therapeutic formulation for administering an active enamel substance, comprising a polymeric matrix, either suitable for cellular growth, in-growth and/or migration, or being cell-occlusive, and an active enamel substance, wherein said matrix is formed by a nucleophilic addition reaction between a strong nucleophile and a conjugated unsaturated bond, or a conjugated unsaturated group.

Preferably, the conjugated unsaturated groups or conjugated unsaturated bonds are acrylates, vinylsulfones, methacrylates, acrylamides, methacrylamides, acrylonitriles, vinylsulfones, 2- or 4-vinylpyridinium, maleimides, or quinones.

The nucleophilic groups are preferably thiol-groups, amino-groups or hydroxyl-groups. Thiol groups are substantially more reactive than unprotonated amine groups. The pH is important in this consideration: the deprotonated thiol is substantially more reactive than the protonated thiol. Therefore, the addition reactions involving a conjugated unsaturation, such as an acrylate or a quinone, with a thiol to convert two precursor components into a polymeric matrix will often be best carried out most quickly and self-selectively at a pH of approximately 8. At pH of approximately 8, a significant number of the thiols of interest are deprotonated (and thus more reactive) and most of the amines of interest are still protonated (and thus less reactive). When a thiol is used as the first precursor molecule, a conjugate structure that is selective in its reactivity for the thiol relative to amines is highly desirable.

Suitable first and second precursor molecules include proteins, peptides, polyoxyalkylenes, poly(vinyl alcohol), poly (ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-d(propylene oxide) block copolymers. A particularly preferred precursor molecule is polyethylene glycol.

Polyethylene glycol (PEG) provides a convenient building block. One can readily purchase or synthesize linear (meaning with two ends) or branched (meaning more than two ends) PEGs and then functionalize the PEG end groups to introduce either a strong nucleophile, such as a thiol, or a conjugated structure, such as an acrylate or a vinylsulfone. When these components are either mixed with each other or with a corresponding component in a slightly basic environment, a matrix will be formed by reaction between the first and the second precursor component. A PEG component can be reacted with a non-PEG component, and the molecular weight or hydrophilicity of either component can be controlled to manipulate the mechanical characteristics, the permeability, and the water content of the resulting biomaterial.

An especially preferred embodiment of the present invention is thus a pharmaceutical and/or therapeutic formulation for administering an active enamel substance, comprising a polymeric matrix, which can be suitable for cellular in-growth and/or migration, or be cell-occlusive, and an active enamel substance, wherein the concentration of said active enamel substance is less than 5 mg/ml formulation and wherein said matrix comprises polyethylene glycol.

As an example, it is straightforward to synthesize peptides that contain two or more cysteine residues, and this component can then readily serve as the first precursor component with nucleophilic groups. For example, a peptide with two free cysteine residues will readily form a matrix when mixed with a PEG tri-vinylsulfone (a PEG having three arms with vinylsulfones at each of its arms) at physiological or slightly higher pH (e.g., 8 to 9). The gelation can also proceed well at even higher pH, but at the potential expense of self-selectivity. When the two liquid precursor components, i.e. the dissolved precursor components, are mixed together, they react over a period of a few seconds to a few minutes to form an elastic gel, consisting of a network of PEG chains, bearing the nodes of the network, with the peptides as connecting links. The peptides can be selected as protease substrates, so as to make the network capable of being infiltrated and degraded by cells, as is done in a protein-based network, such as in a fibrin matrix. Preferably the sequences in the domains are substrates for enzymes that are involved in cell migration (e.g., as substrates for enzymes such as collagenase, plasmin, metalloproteinase (MMP) or elastase), although suitable domains are not be limited to these sequences. One particularly useful sequence is a substrate for the enzyme plasmin. The degradation characteristics of the gels can be manipulated by changing the details of the peptide that serves as the cross-linking nodes. One may make a gel that is degradable by collagenase, but not plasmin, or by plasmin, but not by collagenase. Furthermore, it is possible to make the gel degrade faster or slower in response to such an enzyme, simply by changing the amino acid sequence so as to alter the Km or kcat, or both, of the enzymatic reaction. One can thus make a biomaterial that is biomimetic, in that it is capable of being remodelled by the normal remodelling characteristics of cells, e.g. shows substrate sites for the important protease plasmin. The gelation of the PEG with the peptide is self-selective.

Optionally, biofunctional agents can be incorporated into the matrix to provide chemical bonding to other species (e.g., a tissue surface). Having protease substrates incorporated into the matrix is important when the matrix is formed from PEG vinylsulfone. Other than matrices formed from the reaction of PEG acrylates and PEG thiols, matrices formed from PEG vinylsulfones and PEG thiols do not contain hydrolytically degradable bonds. Therefore, the incorporation of protease substrates allows the matrix to degrade in the body.

The synthetic matrices are operationally simple to form. Two liquid precursors are mixed; one precursor contains a precursor molecule with nucleophilic groups and the other precursor molecule contains the electrophilic groups. Physiological saline can serve as the solvent. Minimal heat is generated by reaction. Therefore, the gelation can be carried out in vivo or in vitro, in direct contact with tissue, without untoward toxicity. Thus polymers other than PEG may be used, either telechelically modified or modified on their side groups.

Consequently, the present invention relates to a pharmaceutical and/or therapeutic formulation for administering an active enamel substance, comprising a polymeric matrix and an active enamel substance, wherein the concentration of said active enamel substance is less than 5 mg/ml formulation, wherein said matrix is preformed, or wherein said matrix is formed in situ.

In one specific aspect of the present invention, a microcapsule is formed, which has an outer shell of a PEG matrix and an inner core comprising aggregated active enamel substances. The microcapsule is formed when a pH is used in a range between pH5 and pH9.5 during polymerisation of PEG in a mixture comprising PEG and active enamel substances. The microcapsule shell is formed by polymerised PEG, which encloses aggregates of active enamel substances. The aggregates of active enamel substance are formed by the pH in a range between pH5 and pH9.5 used for polymerisation. The aggregates of active enamel substances are too large to penetrate pores of the shell of PEG matrix. Thereby, the active enamel substances are not released from the microcapsule until the PEG matrix shell is broken down.

For most healing indications, the rate of cell ingrowth or migration of cells into the matrix in combination with an adapted degradation rate of the matrix is crucial for the overall healing response. The potential of hydrolytically non-degradable matrices to become invaded by cells is primarily a function of network density. If the existing space between branching points or nodes is too small in relation to the size of the cells, or if the rate of degradation of the matrix, which results in creating more space within the matrix, is too slow, a very limited healing response will be observed. Healing matrices found in nature, as e.g. fibrin matrices, which are formed as a response to injury in the body, are known to consist of a very loose network which very easily can be invaded by cells. The infiltration is promoted by ligands for cell adhesion which are an integrated part of the fibrin network.

Matrices made from synthetic hydrophilic precursor molecules, like polyethene glycol, swell in aqueous environment after formation of the polymeric network. In order to achieve a sufficiently short gelling time (between 3 to 10 minutes at a pH of between 7 to 8 and a temperature in a range of 36 to 38° C.) and quantitative reaction during in-situ formation of the matrix in the body, the starting concentration of the precursor molecules must be sufficiently high. Under such conditions, the necessary starting concentrations would lead to matrices too dense for cell infiltration when the matrix is not degradable in aqueous environment. Thus swelling of the polymeric network is important to enlarge and widen the space between the branching points.

Irrespective of the starting concentration of the precursor molecules, hydrogels made from the same synthetic precursor molecules, such as a four arm PEG vinylsulfone and a peptide with SH groups, swell to the same water content in equilibrium state. This means that the higher the starting concentration of the precursor molecules are, the higher the end volume of the hydrogel is when it reaches its equilibrium state. If the space available in the body is too small to allow for sufficient swelling and in particular if the linkage formed from the precursor components are not hydrolytically degradable, the rate of cell infiltration and the healing response will decrease. As a consequence, the optimum between two contradictory requirements for application in the body must be found. Good cell infiltration and subsequent healing responses have been observed with a three-dimensional polymeric network formed from the reaction of a trifunctional branched polymer with at least three arms substantially similar in molecular weight and a second precursor molecule that is at least a bifunctional molecule. The ratio of equivalent weight of the functional groups of the first and second precursor molecules is between 0.9 and 1.1. The molecular weights of the arms of the first precursor molecule, the molecular weight of the second precursor molecule and the functionality of the branching points are selected such that the water content of the resulting polymeric network is between the equilibrium weight % and 92 weight % of the total weight of the polymeric network after completion of water uptake. Preferably the water content is between 93 and 95 weight % of the total weight of the polymeric network and the water after completion of water uptake. Completion of water uptake can be achieved either when the equilibrium concentration is reached or when the space available in the biomaterial does not allow for further volume increase. It is therefore preferred to choose the starting concentrations of the precursor components to be as low as possible. This is true for all swellable matrices but in particular for those matrices which undergo cell-mediated degradation and do not contain hydrolytically degradable linkages in the polymeric network.

The balance between gelling time and low starting concentration in particular for hydrolytically non-degradable gels should be optimized based on the structure of the precursor molecules. In particular, the molecular weight of the arms of the first precursor molecule, the molecular weight of the second precursor molecule and the degree of branching, i.e. the functionality of the branching points, have to be adjusted accordingly. The actual reaction mechanism has a minor influence on this interplay.

Is the first precursor molecule a three or four arm polymer with a functional group at the end of each arm and is the second precursor molecule a linear bifunctional molecule, preferably a peptide containing at least two cysteine groups, then the molecular weight of the arms of the first precursor molecule and the molecular weight of the second precursor molecule are preferably chosen such that the links between the branching points after formation of the network have a molecular weight in the range of between 10 to 13 kDa (under the conditions that the links are linear, not branched), preferably between 11 and 12 kDa. This allows for a starting concentration of the sum of first and second precursor molecules in a range of between 8 to 12 weight %, preferably between 9 and 10 weight % of the total weight of the first and second precursor molecule in solution (before network formation). In case the branching degree of the first precursor component is increased to eight and the second precursor molecule is still a linear bifunctional molecule, the molecular weight of the links between the branching points is preferably increased to a molecular weight of between 18 to 24 kDa. In case the branching degree of the second precursor molecule is increased from linear to a three or four arm precursor component, the molecular weight, i.e. the length of the links increase accordingly.

In a preferred embodiment of the present invention, a composition is chosen including as the first precursor molecule a trifunctional three arm 15 kDa polymer, i.e. each arm having a molecular weight of 5 kDa and as the second precursor molecule a bifunctional linear molecule of a molecular weight in the range of between 0.5 to 1.5 kDa, even more preferably around 1 kDa. Preferably the first and the second precursor component is a polyethylene glycol.

In another preferred embodiment, the first precursor component includes as functional groups conjugated unsaturated groups or bonds, most preferred an acrylate or a vinylsulfone and the functional groups of the second precursor molecule include a nucleophilic group, preferably a thiol or amino groups.

In yet another preferred embodiment of the present invention, the first precursor molecule is a four arm 20 kDa (each arm a molecular weight of 5 kDa) polymer having functional groups at the terminus of each arm and the second precursor molecule is a bifunctional linear molecule of a molecular weight in the range of between 1 to 3 kDa, preferred between 1.5 and 2 kDa. Preferably the first precursor molecule is a polyethylene glycol having vinylsulfone groups and the second precursor molecule is a peptide having cysteine groups. In both preferred embodiments, the starting concentration of the sum of first and second precursor molecule ranges from the 8 to 11 weight %, preferably between 9 and 10 weight % of the total weight of the first and second precursor molecule and water (before formation of polymeric network), preferably between 5 and 8 weight % to achieve a gelling time of below 10 minutes. These compositions have a gelling time at pH 8.0 and 37° C. of about 1-10 minutes, such as between 2-10 minutes, or 3-10 minutes after mixing.

Suitable synthetic gels are e.g. described in WO 03/052091. One such example is an enzymatically degradable gel formed from a four-arm branched PEG functionalized with four vinylsulfone end groups and dithiol peptide of the sequence Gly-Cys-Arg-Asp-(Gly-Pro-Gln-Gly-Ile-Trp-Gly-Gln)-Asp-Arg-Cys-Gly. Another example from WO 03/052091 is a hydrolytically degradable gel formed by mixing an acrylated four-arm polyethylene glycol (MW 15,000) with a linear polyethylene glycol dithiol (MW 3400), which are covalently linked to each other through a Michael type reaction.

When the matrix contains hydrolytically degradable linkages, formed e.g. by the preferred reaction between acrylates and thiols, the network density with regard to cell infiltration is especially important in the beginning, but in aqueous environment the linkages will be hydrolyzed and the network will be loosened, to allow for cell infiltration. With an increase in the overall branching degree of the polymeric network the molecular weight of the interlinks, i.e. the length of the links must increase.

In a specific embodiment of the present invention, a low-concentration formulation comprising an active enamel substance and a polymeric matrix, which is cell-occlusive, is obtained by reaction of at least two precursors in the presence of water. Said formulation is especially preferred for promoting bone formation at an implant site, e.g. in a treatment well known in the art as "Guided Bone Regeneration". Herein, the site where bone formation is desired is separated from the surrounding tissue by a barrier that inhibits non-osteogenic soft tissue cells from entering the site, thus allowing cells from the bone marrow to fill it. The polymeric matrix according to the present invention, forming such a membrane is obtainable by a reaction of two or more precursors, wherein the adjacent cross-points of a chain of precursors are connected by a chain having less than 10000 atoms, such as less than 5000, 1000, 900, 800, 750 atoms, or even more preferred, less than 670 atoms, e.g. between 250-350 atoms, e.g. 300 atoms.

In detail, a first precursor comprises a core which carries 2 or more chains with a conjugated unsaturated terminal group or a conjugated unsaturated terminal bond. The core can be a single atom, such as a carbon or a nitrogen atom, or a small molecule, such as an ethylene oxide unit, a sugar, a multifunctional alcohol, such as a penta-erythritol, glycerine or oligoglycerine, such as a hexaglycerine. The chains are linear polymers or linear or branched alkyl chains, optionally comprising heteroatoms, amide groups or ester groups. Beside the chains, the core may be additionally substituted with linear or branched alkyl residues or polymers which have no terminal conjugated unsaturated groups or bonds. In one presently preferred embodiment, the first precursor has 2 to 10 chains, most preferably, 2 to 6, or 4 to 8 chains. The terminal conjugated unsaturated bonds are preferably maleimide, acrylates, acrylamides, quinines, and 2- or 4-vinylpyridiniums. In an equally preferred embodiment, the first precursor has 2 to 10 chains, most preferably, 3 to 8 chains, such as 3 to 6 chains.

A second precursor comprises a core carrying 2 or more chains each having a thiol group attached to any of the last 20 atoms at the end of the chain. E.g. a cysteine residue may be incorporated into the chain. Preferably, the thiol group is terminal. The core can be a single atom, such as a carbon, or a nitrogen atom, or a small molecule, such as an ethylene oxide unit, a sugar, a multifunctional alcohol, such as a penta-erythritol, glycerine or oligoglycerine, such as a hexaglycerine. The chains are linear polymers, or linear, or branched alkyl chains optionally comprising heteroatoms, amide groups or ester groups. Beside the chains, the core may be additionally substituted with linear or branched alkyl residues, or polymers, which have no terminal conjugated unsaturated groups or bonds. In a preferred embodiment, the second precursor has 2 to 10 chains, most preferably, 2 to 6, or 4 to 8 chains. In an equally preferred embodiment, the second precursor has 2 to 10 chains, most preferably, 3 to 8 chains, such as 3 to 6 chains.

The sum of the chains of the first and the second precursor is greater or equal 5, such as greater or equal 6, preferably greater or equal 8, to obtain a dense three-dimensional network.

Each core of the precursors forms a cross-point. The adjacent cross-points are connected by a chain having less than having less than 10000 atoms, such as less than 5000, 1000, 900, 800, 750 atoms, or even more preferred, less than 670 atoms, e.g. between 250-350 atoms, e.g. 300 atoms . . . wherein said atoms are only the atoms which are in the backbone of the chain, which means not counting substituents or H atoms. Preferably, the number of atoms between two adjacent cross-points is smaller than about 330 atoms, most preferably between 30 and 120 atoms. I.e. the meshes of the resulting three-dimensional network are several orders of magnitude smaller than the dimensions of a cell (1-100 µm) and also smaller than the aggregates formed by active enamel substances at neutral pH, which can e.g. be between 10 nm and 100 µm and would be retained.

In a presently preferred embodiment of the present invention, the meshes of the network are thus between 10 nm-10 µm, i.e. the pores are smaller than, or no larger than approximately on average 1 µm, such as smaller than 500 nm, 400 nm, 300 nm, 250 nm, 200 nm, 100 nm, 75 nm, 50 nm, 10 nm. Preferable sizes of the pores are selected to be between 10 µm and 10 nm, such as between 10 µm and 100 nm, 10 µm and 10 nm, 1 µm and 100 nm, 500 nm and 10 nm, 500 nm and 250 nm, 50 nm and 10 nm etc.

Incorporating the Active Enamel Substance into the Polymeric Matrix

Another, equally preferred embodiment of the present invention, particularly relates to a low-concentration pharmaceutical and/or therapeutic formulation for administering an active enamel substance, comprising a polymeric matrix and an active enamel substances linked to said matrix by a covalent or non-covalent bond. In particular, said active enamel substance can be linked to said matrix due to a nucleophilic addition reaction of at least one cysteine residue in said active enamel substance, which can be a protein, polypeptide or subfragment thereof, to a conjugated unsaturated group of at least one of the components of the matrix, said at least one cysteine residue being either situated in the C-terminus or the N-terminus of said protein, polypeptide or subfragment thereof. This embodiment is especially preferred when said polymeric matrix forms a polymeric network having sufficient inter-polymer spacing to allow for growth, in-growth and/or migration of cells into the matrix. Typically, in this particular embodiment, the crosslinked polymeric matrix forms a gel.

Thus, for the incorporation of an active enamel substance into a matrix formed from synthetic precursor components, an active enamel substance fusion peptide, or any other peptide to be incorporated, can be synthesized with, or chemically altered to comprise at least one additional cysteine group (—SH) as the crosslinkable substrate domain. The free cysteine group then reacts with the conjugated unsaturated group of the precursor component in a Michael type addition reaction. The thiol group of the cysteine can react with a conjugated unsaturated bond on the synthetic polymer to form a covalent linkage.

In one embodiment, said active enamel substance will thus be chemically modified to comprise at least one additional cysteine group (—SH).

The cysteine can be either directly attached to the active enamel substance, or be attached through a linker sequence, which can additionally include an enzymatically degradable amino acid sequence, such as a sequence for proteolytic degradation, or a substrate for polysaccharide degradation and/or a plasmin degradable sequence, or a sequence which is degradable by non-specific hydrolysis, such as an ester bond, so that the active enamel substance can be cleaved from the matrix by e.g. enzymes in substantially the native form.

Degradable Linkages

In general, controlled release of the active enamel substance from the pharmaceutical and/or therapeutical formulation of the present invention reduces the amount of total active enamel substance needed. In particular, this effect is even optimised when its release is controlled by cellular processes. Conservation of active enamel substance and its bioavailability are distinct advantages of exploiting cell specific proteolytic activity over the use of diffusion controlled release devices which characteristically result in the loss of a significant amount of active enamel substance in an initial burst release. In one possible explanation for the strong healing of a bone defect with active enamel substance covalently bound to a matrix, it is deemed important that the active enamel substance is administered locally over an extended period of time (i.e. not just a single pulsed dose) but in a continuous fashion. This is accomplished by a slow degradation, through either enzymatic cleavage or hydrolytic cleavage of the matrix. In this way, the molecule is then delivered through a pseudo-pulsed effect that occurs over a sustained period of time. E.g. when a progenitor cell Infiltrates the matrix, it will encounter an active enamel substance molecule and can thereupon differentiate into a preosteoblast. However, if that particular cell does not continue to liberate bound active enamel substance from the matrix, it will effectively convert into an osteoblast and begin producing bone matrix. Finally, the therapeutic effects of the active enamel substance is localized to the defect region and is thus subsequently magnified.

Any of the monomers, polymers, proteins, polypeptides, or subfragments thereof, forming the matrix can be modified through inclusion of degradable linkages. Typically, these will be enzyme cleavage sites, such as the site for cleavage by thrombin.

Moreover, fusion proteins or peptide chimeras of active enamel substances, which are cross-linked to the matrix, may contain a degradable site between the bioactive protein in a first domain and an attachment site in a second domain (e.g. a cysteine, a factor XIIIa substrate or heparin-binding domain). These degradable sites may degrade by non-specific hydrolysis (i.e. an ester bond) or they may be substrates for specific enzymatic degradation (either proteolytic or polysaccharide degradation).

The degradation sites allow the active enamel substance to be released with little or no modification to the primary protein sequence, which may result in higher activity of the active enamel substance. Further, the degradable sites allow for more specific release of the active enamel substance from matrices, such as fibrin gels. For example, degradation based on enzymatic activity allows for the release of an active enamel substance to be controlled by a cellular process, such as localized proteolysis, rather than by diffusion of the active enamel substance from some porous materials. The degradable site or linkage is cleaved by enzymes released from cells which invade the matrix. This allows active enamel substances to be released at different rates within the same material depending on the location of cells within the material. Cell specific proteolytic activity is vital in those applications, which occur over long periods of time.

Enzymes that can be used for proteolytic degradation are numerous. Proteolytically degradable sites include substrates for collagenase, plasmin, elastase, stromelysin, or plasminogen activators. Exemplary substrates are listed in table 2. P1-P5 denote amino acids 1-5 positions toward the amino terminus of the protein from the site were proteolysis occurs. P1'-P4' denote amino acids 1-4 positions toward the carboxy terminus of the protein from the site where proteolysis occurs.

In another preferred embodiment, an oligo-ester domain could be inserted between the first and the second domain. This could be accomplished using an oligo-ester such as oligomers of lactic acid.

Non-enzymatic degradation substrate can consist of any linkage which undergoes hydrolysis by an acid or base catalyzed mechanism. These substrates can include oligo-esters such as oligomers of lactic or glycolic acid. The rate of degradation of these materials can be controlled through the choice of oligomer.

Polysaccharide Substrates

Enzymatic degradation can furthermore occur with polysaccharide substrates for enzymes such as heparinase, heparitinase, and chondroitinase ABC. Each of these enzymes have polysaccharide substrates. By virtue of the presence of heparin in all of the heparin-binding systems, the substrate for heparinase is already built into these systems.

Thus, equally envisioned is a pharmaceutical and/or therapeutic formulation for administering an active enamel substance, comprising a polymeric matrix and an active enamel substance, wherein the concentration of said active enamel substance is 5 mg/ml formulation or less, and wherein said active enamel substance is covalently or non-covalently bound to said matrix through at least one heparin binding fragment.

A proteolytic substrate can be added during peptide synthesis of either the active enamel substance chimera or the heparin-active enamel substance chimera. The heparin-binding active enamel substance chimera could be modified to contain a proteolytic degradation sequence by inserting a protease substrate, such as the sequence for plasmin (see e.g. Table 2), between the factor XIIIa substrate and the heparin-binding domain. A substrate with a high $K_m$ and a low $k_{cat}$ could be used to slow cleavage while occupying active sites of the protease. The cleavage substrates other than those for plasmin could be used to allow release of the active enamel substance to be independent of matrix degradation.

Concomittantly, an oligo-ester domain could be inserted between the second domain such as the factor XIIIa substrate and the first domain, which is either the active enamel substance or the heparin-binding domain, or the heparin domain of the chimera during the peptide synthesis step as well. This could be accomplished using an oligo-ester such as oligomers of lactic acid.

A non-enzymatic degradation substrate can consist of any linkage which undergoes hydrolysis by an acid or base catalyzed mechanism. These substrates can include oligo-esters

TABLE 2

Sample substrate sequences for protease

| Protease | P5 | P4 | P3 | P2 | P1 | P1' | P2' | P3' | P4' | Reference |
|---|---|---|---|---|---|---|---|---|---|---|
| Plasmin | | | L | I | K | M | K | P | | Takagi and Doolittle (1975) Biochem. 14: 5149-5156 |
| Plasmin | | | N | F | K | S | Q | L | | Takai and Dolittle, 1975 |
| Stromelysin | Ac | G | P | L | A | L | T | A | L | Smith et al., (1995). J. Biol. Chem. 270: 6440-6449 |
| Stromelysin | | Ac | P | F | E | L | R | A | NH$_2$ | Smith et al., 1995 |
| Elastase | | | Z-(?) | A | A | F | A | NH$_2$ | | Besson et al., (1996) Anal. Biochem. 237: 216-223 |
| Collagenase | | | G | P | L | G | I | A | G | P | Netzel-Arnett et al., (1991) J. Biol. Chem., 266: 6747-6755 |
| t-PA | P | H | Y | G | R | S | G | G | | Coombs et al., (1998) J. Biol. Chem. 273-4323-4328 |
| u-PA | P | G | S | G | R | S | A | S | G | Coombs et al., 1998 | such as oligomers of lactic or glycolic acid. The rate of degradation of these materials can be controlled through the choice of oligomer.

Heparin; Heparin Binding Peptides

A polymeric matrix according to the present invention can furthermore be modified through the inclusion of heparin and/or heparin binding fragments, which bind directly or indirectly to proteins which bind to heparin. In the latter case, the proteins can bind to heparin, which is then available for binding to an active enamel substance which includes a heparin binding site, or the active enamel substance can itself contain a heparin portion which is bound by certain heparin-binding active enamel substances. These can be attached to the matrix material using standard techniques, as discussed in more detail below.

One envisioned embodiment of the present application is thus a low-concentration pharmaceutical and/or therapeutic formulation for administering an active enamel substance, comprising a polymeric matrix, either suitable for cellular growth or in-growth, or cell-occlusive, and an active enamel substance, wherein the concentration of said active enamel substance is less than 5 mg/ml formulation, and wherein said matrix is modified through the inclusion of at least one heparin and/or at least one heparin binding fragment.

In a preferred embodiment, heparin is attached to fibrin gels non-covalently using a two-part system consisting of a peptide chimera and heparin itself. The peptide chimera consists of two domains, a factor XIIIa substrate and a polysaccharide-binding domain. Once the peptide chimera is cross-linked into the fibrin gel, it attaches the heparin (or other polysaccharides) by non-covalent interactions.

Numerous proteins have been found to have heparin-binding affinity. Examples can be found in Table 3 below.

the matrix have been shown to control cell adhesion, spreading, migration and differentiation (Carey, Annual Review of Physiology, 53:161-177, 1991). Some of the specific proteins that have been shown to be particularly active include laminin, vitronectin, fibronectin, fibrin, fibrinogen and collagen (Lander, Journal of Trends in Neurological Science, 12:189-195, 1989). Many studies of laminin have been conducted, and it has been shown that laminin plays a vital role in the development and regeneration of nerves in vivo and nerve cells in vitro (Williams, Neurochemical Research, 12:851-869, 1987), as well as in angiogenesis.

Some of the specific sequences that directly interact with cellular receptors and cause either adhesion, spreading or signal transduction have been identified.

Laminin, a large multidomain protein (Martin, Annual Review of Cellular Biology, 3:57-85, 1987), has been shown to consist of three chains with several receptor-binding domains. These receptor-binding domains include the YIGSR sequence of the laminin B1 chain (Graf, et al., Cell, 48:989-996, 1987; Kleinman, et al., Archives of Biochemistry and Biophysics, 272:39-45, 1989; and Massia, et al, J. of Biol. Chem., 268:8053-8059, 1993), LRGDN of the laminin A chain (Ignatius, et al., J. of Cell Biology, 111:709-720, 1990) and PDGSR of the laminin B1 chain (Kleinman, et al, 1989). Several other recognition sequences for cells have also been identified. These include IKVAV of the laminin A chain (Tashiro, et al., J. of Biol. Chem., 264:16174-16182, 1989) and the sequence RNIAEIIKDI of the laminin B2 chain (Liesi, et al., FEBS Letters, 244:141-148, 1989).

In a further preferred embodiment, peptide sites for cell adhesion are incorporated into the matrix, namely peptides that bind to adhesion-promoting receptors on the surfaces of cells into the biomaterials of the present invention. Such

TABLE 3

Heparin-binding sequences

| Protein | Heparin-binding domain | Reference |
| --- | --- | --- |
| Anti-thrombin III | K(βA)FAKLAARLYRKA | Tyler-Cross, R., et. Protein Science. 3: 620-627 |
| Platelet Factor 4 | YKKIIKKL | Zucker and Katz, (1991). Exper. Biol. Med.: 693-702 |
| Neural Cell | KHKGRDVILKKDVR | Kallapur, et al, Adhesion Molecule (1992) J. Neurosci. Res. 33: 538-548 |
| Fibronectin | YEKPGSPPREVVPRPRPCV KNNQKSEPLIGRKKT | Haugen, et al., (1992). J. Neurosci. 12: 2034-2042 |
| bFGF (basic fibroblast growth factor) | KDPKRL YRSRKY | SwissPROT: P09038 |
| aFGF (acidic fibroblast growth factor) | YKKPKL | SwissPROT: P05230 |
| LPL (lipoprotein lipase) | AKRSSKM CRKRCN | Hata, et al., J. Biol. Chem. 268: 8447-8457 |

In an alternatively envisioned embodiment, the active enamel substance in itself shows affinity for binding substrates that have heparin-binding affinities, such as the substances exemplified in table 3. In such an embodiment, the active enamel substance is bound into the polymeric matrix either covalently or non-covalently as described above, thus providing a heparin-like domain for non-covalent interactions with any other substance with heparin-binding affinity.

Cell Attachment Sites

Cells interact with their environment through protein-protein, protein-oligosaccharide and protein-polysaccharide interactions at the cell surface. Extracellular matrix proteins provide a host of bioactive signals to the cell. This dense network is required to support the cells, and many proteins in adhesion promoting peptides can be selected from the group as described above. Particularly preferred are the RGD sequence from fibronectin, and the YIGSR sequence from laminin. Incorporation of cell attachment sites are a particularly preferred embodiment with synthetic matrices, but can also be included with some of the natural matrices. The incorporation can be done, for example, simply by mixing a cysteine-containing cell attachment peptide with the precursor molecule including the conjugated unsaturated group, such as PEG acrylate, PEG acrylamide or PEG vinylsulfone a few minutes before mixing with the remainder of the precursor component including the nucleophilic group, such as thiol-containing precursor component. If the cell attachment site does not include a cysteine, it can be chemically synthesized to include one. During this first step, the adhesion-promoting peptide will become incorporated into one end of the precursor multiply functionalized with a conjugated unsaturation; when the remaining multithiol is added to the system, a cross-linked network will form. Another important implication of the way that networks are prepared here, is the efficiency of incorporation of pendant bioactive ligands such as adhesion signals. This step has to be quantitative, since, for example, unbound ligands (e.g. adhesion sites) could inhibit the interaction of cells with the matrix. The derivatization of the precursor with such pendant oligopeptides is conducted in a first step in stoichiometric large excess (minimum: 40-fold) of multiarmed electrophilic precursors over thiols and is therefore definitely quantitative. Aside from preventing unwanted inhibition, this accomplishment is biologically even more significant: cell behavior is extremely sensitive to small changes in ligand densities and a precise knowledge of incorporated ligands helps to design and understand cell-matrix interactions. Summarized, the concentration of adhesion sites covalently bound into the matrix significantly influences the rate of cell infiltration. For example, for a given hydrogel, a RGD concentration range can be incorporated into the matrix with supports cell ingrowth and cell migration in an optimal way.

A presently preferred embodiment is thus a low-concentration pharmaceutical and/or therapeutic formulation for administering an active enamel substance, comprising a polymeric matrix suitable for cellular growth or in-growth, and an active enamel substance, wherein the concentration of said active enamel substance is less than 5 mg/ml formulation, and wherein said matrix is modified through the inclusion of RGD. See for example examples 2 and 4 in the experimental section.

Methods of Use

The present invention provides a low-concentration formulation of active enamel substances for hard and soft tissue repair, regeneration or remodelling, in particular for bone and tooth growth, using natural and/or synthetic matrices having an active enamel substance releasable incorporated and/or enclosed therein. The matrices are biocompatible and/or biodegradable and can be formed in vitro or in vivo at the time of implantation. The active enamel substance can be incorporated and/or enclosed into the matrices and retains its full bioactivity. What is more, as outlined above, the active enamel substance can be releasable incorporated, using techniques that provide control over how and when and to what degree the active enamel substance is released, so that the matrix can be used for tissue repair directly or indirectly, using the matrix as a controlled release vehicle.

The new low-concentration pharmaceutical, cosmetic and/or therapeutic formulations described herein can be used for repair, regeneration, and/or remodelling of tissues, and/or release of an active enamel substance, prior to or at the time of implantation. In some embodiments it will be desirable to induce crosslinking at the site of administration to conform the matrix to the tissue at the implantation site. In other embodiments, it will be convenient to prepare the matrix prior to implantation.

Cells can also be added to the pharmaceutical and/or therapeutic formulations prior to or at the time of implantation, or even subsequent to implantation, either at or subsequent to crosslinking of the polymer to form the matrix. This may be in addition to or in place of crosslinking the matrix to produce interstitial spacing designed to promote cell proliferation or in-growth.

Although in most cases it will be desirable to introduce the pharmaceutical and/or therapeutic formulations to promote cell growth or proliferation, in some potential scenarios, the active enamel substances will be used to inhibit the rate of cell proliferation. A specific application is to inhibit the formation of adhesion following surgery and to inhibit the in-growth of fibroblasts into a wound bed following the placement of an implant.

In one particular aspect, the new and improved low-concentration formulation of enamel matrix, enamel matrix derivatives and/or enamel matrix proteins described herein is intended to be used as a medicament, such as a therapeutic, prophylactic and/or as cosmetic agent, in particular for use in tissue repair, regeneration and/or remodelling, for inducing binding between parts of living mineralized tissue, for bonding a piece of living mineralized tissue to a bonding site on a piece of other living tissue, for improving the healing of a wound in skin or mucosa, for preventing or treating an infection or an inflammatory condition, for the formation or regeneration of dentin, for promoting the take of a graft, for treating epithelially derived benign, semi-malignant or malignant neoplasms, for the induction of apoptosis, or for filling a wound cavity and/or tissue defect following a procedure and/or trauma, such as cytoreductive surgery.

In a second aspect, such a pharmaceutical and/or therapeutic formulation will be employed for the manufacture of a medicament for repairing mineralized tissue, such as bone, cartilage and teeth, for tissue repair of non-mineralized tissue, such as soft tissue and mucosa, for the treatment of a condition involving inflammation and/or infection, for the formation or regeneration of dentin, for promoting the take of a graft, for treating epithelially derived benign, semi-malignant or malignant neoplasms, for the induction of apoptosis, or for filling a wound cavity and/or tissue defect following a procedure and/or trauma, such as cytoreductive surgery.

Applying the new and improved low-concentration formulation of enamel matrix, enamel matrix derivatives and/or enamel matrix proteins described herein in a periodontal dehiscence model in pigs (see example 5 in the experimental section) for healing and regeneration of periodontal tissue, in particular for regrowth of mineralized tissue, it was surprisingly found that the morphology of the regenerated bone structure was different from the structure regenerated when using enamel matrix derivative in a classical high concentration formulation (30 mg/ml in PGA). Thus it was found that the new formulation for the first time allows for guided neogenesis of mineralized tissue, such as guided bone growth or bone regrowth in a mammalian body.

Without wanting to limit the present invention to a specific scientific theory, it is envisioned that the newly formed bone structure was formed inside the pharmaceutical and/or therapeutic formulation for administering an active enamel substance, comprising a polymeric matrix, which is suitable for cellular in-growth and/or migration, and an active enamel substance. Thus, the volume, shape and position of this novel matrix can be used to model volume, shape and position of the corresponding bone generation, allowing for new and complex applications of such matrixes, irrespective of the actual concentration of active enamel substance in such a formulation. The skilled artisan will apprehend that said concentration of enamel matrix can be adjusted to best suit each specific need.

Possible new medical and/or dental applications for the pharmaceutical and/or therapeutic formulation for administering an active enamel substance of the present invention, comprising a polymeric matrix, which is suitable for cellular in-growth and/or migration, and an active enamel substance are e.g. treatment of large or complex defects in teeth, such as furcation defects, or regrowth of lost bone structures in the skeleton, or in the joints of a mammalian body. It is further envisioned that the formulation can be used for guided bone neogenesis or regrowth into a specific shape in vivo, in situ, or outside the mammalian body, as well as in a non-terminal location of the mammalian body, whereupon such a new bone structure could easily be used for implanting into the mammalian body.

In a presently preferred embodiment, a formulation of active enamel substances, to be employed for the above outlined new medical indication, comprises polyethylene glycol and a concentration of said active enamel substance which is less than 5 mg/ml formulation. Nonetheless, such a new medical indication can of course also include the use of a formulation of active enamel substances, comprising polyethylene glycol or any other polymeric matrix suitable for cellular in-growth and/or migration, wherein the concentration of the active enamel substance is more than 5 mg/ml, such as e.g. more than 10, 20 or 30 mg/ml, or even more. Further envisioned is a kit comprising a pharmaceutical and/or therapeutic formulation according to the present invention and EMDOGAIN® for a simultaneous application of both formulations, and the use of such a combinatorial kit as a medicament.

Advantages of Sustained Release Formulations of the Present Invention

The pharmaceutical and/or therapeutic formulations of the present invention comprising a polymeric matrix and an active enamel substances can be used as sustained release formulations. The biological half life of proteins/polypeptides is often short and therefore the biological activity of them rapidly lost when administered to the body. Also, with common formulations, in contrast to the herein described sustained release formulations, there is an initial burst of activity of the substance due to the large amount of substance initially released after administration, whereafter the biological activity decreases by time. In contrast, by using the pharmaceutical and/or therapeutic formulations of the present invention, the release of the active enamel substances can be controlled both with regards to time of release and concentration released. Also, by using the pharmaceutical and/or therapeutic formulations of the present invention, the release of the active enamel substances is a localised release, where the release occurs in a controlled manner at the desired body site. The formulations of the present invention also allow an even amount of the active enamel substances to be released over prolonged time periods, even for days and weeks if desirable. Thereby the wound healing process is improved.

The time during which the active enamel substance is released and the amount released per time unit can be adjusted by changing the composition of the pharmaceutical and/or therapeutic formulation regarding concentration of polymer, degree of crosslinking of the polymer and the active enamel substance, concentration of active enamel substances in the formulation, incorporation of enzyme cleavage sites and other biologically active substances which affect the rate of degradation of the polymer network as described in other places in this text. Thereby, the release profile can be adjusted for each specific application as desired.

What is more, as some of the new formulations described herein are more formstable than the classical formulations of enamel matrix derivatives in e.g. PGA gel, and when they are also designed to be suitable for cellular ingrowth, they can for the first time be used for guiding a particular regrowth of mineralized tissue into a specific shape, volume and/or localisation.

Methods of Application

In one embodiment, the pharmaceutical and/or therapeutic formulation is gelled in situ in or on the body. In another embodiment, the pharmaceutical and/or therapeutic formulation can be preformed outside the body and then applied in the preformed shape.

As described above, the matrix material can be made from synthetic or natural precursor components. Irrespective of the kind of precursor component used, the precursor components should be separated prior to application of the mixture to the body to prevent combination or contact with each other under conditions that allow polymerization or gelation of the components. To prevent contact prior to administration, a kit which separates the compositions from each other may be used. Upon mixing under conditions that allow polymerization; the compositions form an active enamel substance supplemented three dimensional network. Depending on the precursor components and their concentrations, gelling can occur quasi-instantaneously after mixing.

In one embodiment the matrix is formed from fibrinogen. Fibrinogen, through a cascade of various reactions gels to form a matrix, when brought in contact with thrombin and a calcium source at appropriate temperature and pH. The three components, fibrinogen, thrombin, and the calcium source, should be stored separately. However, as long as at least one of the three components is kept separated the other two components can be combined prior to administration. Fibrinogen can be dissolved (which may contain additionally aprotinin to increase stability) in a buffer solution at physiological pH (in a range from pH 6.5 to 8.0, preferably from pH 7.0 to 7.5) and stored separately from a solution of thrombin in a calcium chloride buffer (e.g. concentration range of from 40 to 50 mM). The buffer solution for the fibrinogen can be a histidine buffer solution at a preferred concentration of 50 mM including additionally NaCl at a preferred concentration of 150 mM or TRIS buffer saline (preferably at a concentration of 33 mM). In a preferred embodiment, a kit, which contains an active enamel substance, fibrinogen, thrombin, and a calcium source, is provided. Optionally, the kit may contain a crosslinking enzyme, such as Factor XIIIa. The active enamel substance can be a fusion protein containing a bioactive domain of an active enamel substance, a substrate domain for a crosslinking enzyme and a degradation site between the substrate domain and bioactive domain. The fusion protein may be present in either the fibrinogen or the thrombin solution. In a preferred embodiment the fibrinogen solution contains the fusion protein.

The solutions are preferably mixed by a two way syringe device, in which mixing occurs by squeezing the contents of both syringes through a mixing chamber and/or needle and/or static mixer. Other, equally preferred options are to add the 2 solutions to a container, mix them therein, transfer to e.g. a syringe and apply thereafter. Optimally, both solutions can be dissolved in a slightly acidic buffer in syringe 1, then be attached to a syringe with a female luer containing base (and alternatively viscosity modifier) and mixed by syringe-syringe mixing.

In a presently preferred embodiment both fibrinogen and thrombin are stored separately in lyophilised form. Either of the two can contain the fusion protein. Prior to use, the tris or histidine buffer is added to the fibrinogen, the buffer may additionally contain aprotinin. The lyophilized thrombin is dissolved in the calcium chloride solution. Subsequently, the fibrinogen and the thrombin solutions are placed in separate containers/vials/syringe bodies and mixed by a two way connecting device, such as a two-way syringe. Optionally, the containers/vials/syringe bodies are bipartited thus having two chambers separated by an adjustable partition which is perpendicular to the syringe body wall. One of the chambers contains the lyophilised fibrinogen or thrombin, while the other chamber contains an appropriate buffer solution. When the plunger is pressed down, the partition moves and releases the buffer into the fibrinogen chamber to dissolve the fibrinogen. Once both fibrinogen and thrombin are dissolved, both bipartite syringe bodies are attached to a two way connecting device and the contents are mixed by squeezing them through the injection needle attached to the connecting device. Optionally, the connecting device contains a static mixer to improve mixing of the contents.

In another, equally preferred embodiment, the fibrinogen is diluted eight fold and thrombin is diluted 20 fold prior to mixing. This ratio results in a gelation time of approximately one minute.

In a further embodiment, the polymeric matrix comprised in the low-concentration formulation of the present invention is formed from synthetic precursor components capable of undergoing a Michael addition reaction. Since the nucleophilic precursor component (the multithiol) only reacts with the multiacceptor component (the conjugated unsaturated group) at basic pH, the three components which have to be stored separately prior to mixing are: the base, the nucleophilic component and the multiacceptor component. Both the multiacceptor and the multithiol component can be stored as a solution in buffers or in acids. PEG-acrylate is usually stored dry. Thus, alternatively, both PEGs are stored dry and dissolved in basic buffer prior to use (as documented in example 2), or the PEG-thiol is stored in acidic buffer and mixed with the PEG-acrylate prior to use, followed by mixing with a base (see example 3). Both of the compositions can include the cell attachment site and additionally the active enamel substance. Thus, the first composition of the system can for example include the solution of the nucleophilic component and the second composition of the system can include the solution of the multiacceptor component. Either or both of the two compositions can include the base. In another embodiment, the multiacceptor and the multithiol can be included as solution in the first composition and the second composition can include the base. Connecting and mixing occurs in the same way as previously described for fibrinogen. The bipartite syringe body is equally suitable for the synthetic precursor components. Instead of fibrinogen and thrombin the multiacceptor and multithiol components are stored in pulverized form in one of the chamber and the other chamber contains the basic buffer. Other, equally preferred options are to add the 2 solutions to a container, mix them therein, transfer to e.g. a syringe and apply thereafter. Optimally, both PEGs can be dissolved in a slightly acidic buffer in syringe 1, then be attached to a syringe with a female luer containing base (and alternatively viscosity modifier) and mixed by syringe-syringe mixing.

DEFINITIONS

"Biomaterial" as generally used herein refers to a material intended to interface with biological systems to evaluate, treat, augment, or replace any tissue, organ or function of the body depending on the material either permanently or temporarily. The terms "biomaterial" and "matrix" are used synonymously herein and mean a crosslinked polymeric network which, depending of the nature of the matrix, can be swollen with water but not dissolved in water, i.e. form a hydrogel which stays in the body for a certain period of time fulfilling certain support functions for traumatized or defect soft and/or hard tissue.

The term "protein matrix" means a matrix formed by crosslinking of protein precursor molecules to a polymeric network ionically, covalently, or by combinations thereof, or by swelling one or more polymeric material(s), i.e. matrices, to form a polymeric network.

"Polysaccharide matrix" is used to describe a matrix formed by crosslinking of polysaccharide precursor molecules to a polymeric network ionically, covalently, or by combinations thereof, or by swelling one or more polymeric material(s), i.e. matrices, to form a polymeric network.

By "synthetic matrix" a matrix is meant which is formed by crosslinking synthetic precursor molecules to a polymeric network ionically, covalently, or by combinations thereof, or by swelling one or more polymeric material(s), i.e. matrices, to form a polymeric network.

The term "polymeric matrix" is used to include either of the protein, polysaccharide and synthetic matrices described above. A polymer per se is a large molecule formed by the union of at least 5 monomers.

As used herein, "enamel matrix" means the precursor of enamel which can be obtained from any relevant natural source, i.e. a mammal in which teeth are under development. A suitable source is developing teeth from slaughtered animals such as, e.g., calves, pigs or lambs. Another source is e.g. fish skin. In the present context, the term "an active enamel substance" is used to encompass enamel matrix derivatives and/or enamel matrix proteins nondiscriminant of their source. The terms "enamel matrix", enamel matrix derivative" (EMD), "enamel matrix protein" etc. are not to be confused with the polymer matrices described above.

"Strong nucleophile" as generally used herein refers to a molecule which is capable of donating an electron pair to an electrophile in a polar-bond forming reaction. Preferably the strong nucleophile is more nucleophilic than water at physiologic pH. Examples of strong nucleophiles are thiols and amines.

"Conjugated unsaturated bond" as generally used herein refers to the alternation of carbon-carbon, carbon-heteroatom or heteroatom-heteroatom multiple bonds with single bonds, or the linking of a functional group to a macromolecule, such as a synthetic polymer or a protein. Such bonds can undergo addition reactions.

"Conjugated unsaturated group" as generally used herein refers to a molecule or a region of a molecule, which contains an alternation of carbon-carbon, carbon-heteroatom or heteroatom-heteroatom multiple bonds with single bonds, which has a multiple bond which can undergo addition reactions. Examples of conjugated unsaturated groups include, but are not limited to vinyl sulfones, acrylates, acrylamides, quinones, and vinylpyridiniums, for example, 2- or 4-vinylpyridinium and itaconates.

"Synthetic precursor molecules" as generally used herein refers to molecules which do not exist in nature.

"Naturally occurring precursor components or polymers" as generally used herein refers to molecules which could be found in nature.

"Functionalize" as generally used herein, refers to modifying a molecule in a manner that results in the attachment of a functional group or moiety. For example, a molecule may be functionalized by the introduction of a molecule which makes the molecule a strong nucleophile or a conjugated unsaturation. Preferably a molecule, for example PEG, is functionalized to become a thiol, amine, acrylate, or quinone. Proteins, in particular, may also be effectively functionalized by partial or complete reduction of disulfide bonds to create free thiols.

"Functionality" as generally used herein refers to the number of reactive sites on a molecule.

"Functionality of the branching points" as generally used herein refers to the number of arms extending from one point in the molecule.

"Adhesion site or cell attachment site" as generally used herein, refers to a peptide sequence to which a molecule, for example, an adhesion-promoting receptor on the surface of a cell, binds. Examples of adhesion sites include, but are not limited to, the RGD sequence from fibronectin, and the YIGSR sequence from laminin. Preferably adhesion sites are incorporated into the biomaterial by including a substrate domain crosslinkable to a matrix.

"Biological activity" as generally used herein, refers to functional events mediated by a protein of interest. In some embodiments, this includes events assayed by measuring the interactions of a polypeptide with another polypeptide. It also includes assaying the effect which the protein of interest has on cell growth, differentiation, death, migration, adhesion, interactions with other proteins, enzymatic activity, protein phosphorylation or dephosphorylation, transcription, or translation.

"Regenerate" as generally used herein means to grow back a portion or all of something, such as hard or soft tissue, in particular bone or tooth tissue.

"Multifunctional" as generally used herein refers to more than one electrophilic and/or nucleophilic functional group per molecule (i.e. monomer, oligo- and polymer).

"Self selective reaction" as generally used herein means that the first precursor component of a composition reacts much faster with the second precursor component of the composition and vice versa than with other compounds present in a mixture or at the site of the reaction. As used herein, the nucleophile preferentially binds to a electrophile and an electrophile preferentially binds to a strong nucleophile, rather than to other biological compounds.

"Cross-linking" as generally used herein means the formation of covalent linkages. However, it may also refer to the formation of non-covalent linkages, such as ionic bonds, or combinations of covalent and non-covalent linkages.

A "gel" is a material in which a crosslinked polymer network is swollen to a finite extent by a continuous phase of an aqueous solution.

"Polymeric network" as generally used herein means the product of a process in which substantially all of the monomers, oligo- or polymers are bound by intermolecular covalent linkages through their available functional groups to result in one huge molecule.

"Physiological" as generally used herein means conditions as they can be found in living vertebrates. In particular, physiological conditions refer to the conditions in the human body such as temperature, pH, etc. Physiological temperatures means in particular a temperature range of between 35° C. to 42° C., preferably around 37° C.

"Crosslink density" as generally used herein refers to the average molecular weight between two crosslinks ($M_c$) of the respective molecules.

"Equivalent weight" as generally used herein refers to mmol of functional group/g of substance.

"Swelling" as generally used herein refers to the increase in volume and mass by uptake of water by the biomaterial. The terms "water-uptake" and "swelling" are used synonymously throughout this application.

"Equilibrium state" as generally used herein as the state in which a hydrogel undergoes no mass increase or loss when stored under constant conditions in water or buffer.

In the present context, the term "cell-occlusive" is used to describe the characteristics of a polymeric matrix which is able to close off or block cells from a compartment formed by said matrix, in a way that cells can essentially not cross into or out of said compartment. E.g. this barrier-like function can be facilitated by a polymeric matrix that is virtually shaped as a membrane and that has a pore-size, which is smaller than the cells that it is intended to block from entering or leaving said compartment. Understandably, the exact dimensions of the pores are dependent on the size of the cells that are to be blocked off.

EXPERIMENTAL SECTION

Example 1

Tooth Supporting Tissue Regeneration in Monkey

The aim of the present study was to assess the effect of different concentrations of Enamel Matrix Derivative admixed with the vehicle Propylene Glycol Alginate, on regeneration of tooth supporting tissues, as well as to assess its biological safety. The Enamel Matrix Derivative used herein is made up of the low-molecular weight protein fraction of a standard Enamel Matrix Preparation.

Materials and Methods

Test substance: Enamel Matrix Derivative, batch PEU 801.
Source; Enamel matrix was isolated from porcine tooth germs, homogenized and the low-molecular weight protein fraction extracted.
Vehicle; Propylene Glycol Alginate solution 2.5% w/v, batch PGA 803.
Storage of test substance and vehicle; The test substance and the vehicle were stored at −18° C. The bottles containing the substance and vehicle were allowed to equilibrate with room temperature before use.
Administration of test preparation; The substance was dissolved with the vehicle aseptically under a laminar air flow hood and used individually for the monkeys. Final concentrations of the test substance were determined prior to the experiment and expressed as mg protein/ml reconstituted solution (table 4).
Animals: Seven (7) monkeys (*Macaca fasclcularis*), 3- to 4-years old were purchased from the Primate Research Center, National Bacteriological Laboratory, Solna, SWEDEN, where the animals were housed throughout the experiment. Each animal was given an individual identification code. They were kept individually in cages in a controlled environment:
Temperature 18-22° C.
Relative humidity 40-70%
Light between 6 am and 6 pm
They were given free access to a standard monkey Chow (R3, Ewos A B, Sodertälje, Sweden) and tap water. The diet was daily supplemented with fresh fruit.
Experimental designs: Teeth in each monkey were assigned to test or control groups. Periodontal surgery, according to the modified Widman-technique was performed. The test preparations were applied to the root surfaces of the test teeth before repositioning and suturing of the flaps. The control teeth were sham operated but did not receive any test preparation. In a step-wise fashion the procedure was as follows:
1. Thirty minutes before surgery, the vials containing the test substance were prepared. One vial of test substance was used for each group of two teeth. Twenty minutes was allowed for the test substance to dissolve. The solution was withdrawn with a 3 ml syringe and allowed to settle to the plunger. Air was carefully removed from the syringe by pushing the plunger.

2. The animals were anesthetized with sodium pentobarbital and the area selected for surgery was anesthetized locally and disinfected. A full-thickness flap (mucoperiosteal flap) was raised on the oral and facial sides of the teeth.
3. The buccal bone plate was removed with a large round burr under constant rinsing with sterile saline. The area was thoroughly rinsed with sterile saline and the exposed dental roots etched for 30 seconds with 37% ortho-phosphoric acid or citric acid (pH 1). A final rinse with sterile saline was given. Excess fluid was swabbed off.
4. The test preparations were immediately applied starting in the most apical part of the bone defects and the entire exposed root surfaces was covered.
5. The flaps were repositioned and sutured together. Periodontal dressing was not used.
6. The local clinical appearance around the control and experimental teeth and general behaviour of the monkeys were recorded daily.

Terminal studies; After fifty-six days (8 weeks), the monkeys were killed by an overdose of sodium pentobarbital and the control and rest teeth were evaluated histologically.

Histological preparation: The experimental and control teeth together with surrounding alveolar bone and soft tissue were dissected out and used for light microscopic examination. The specimens were fixed in cold 10% buffered formalin for 48 hours, demineralised in 5% formic acid, embedded in paraffin, and sectioned parallel to the long axis of the teeth in a bucco-lingual direction. The sections were cut step-serially at levels 20 μm apart and stained with hematoxylin and eosin. They were then examined in transmitted ordinary and polarized light.

Figure 1:
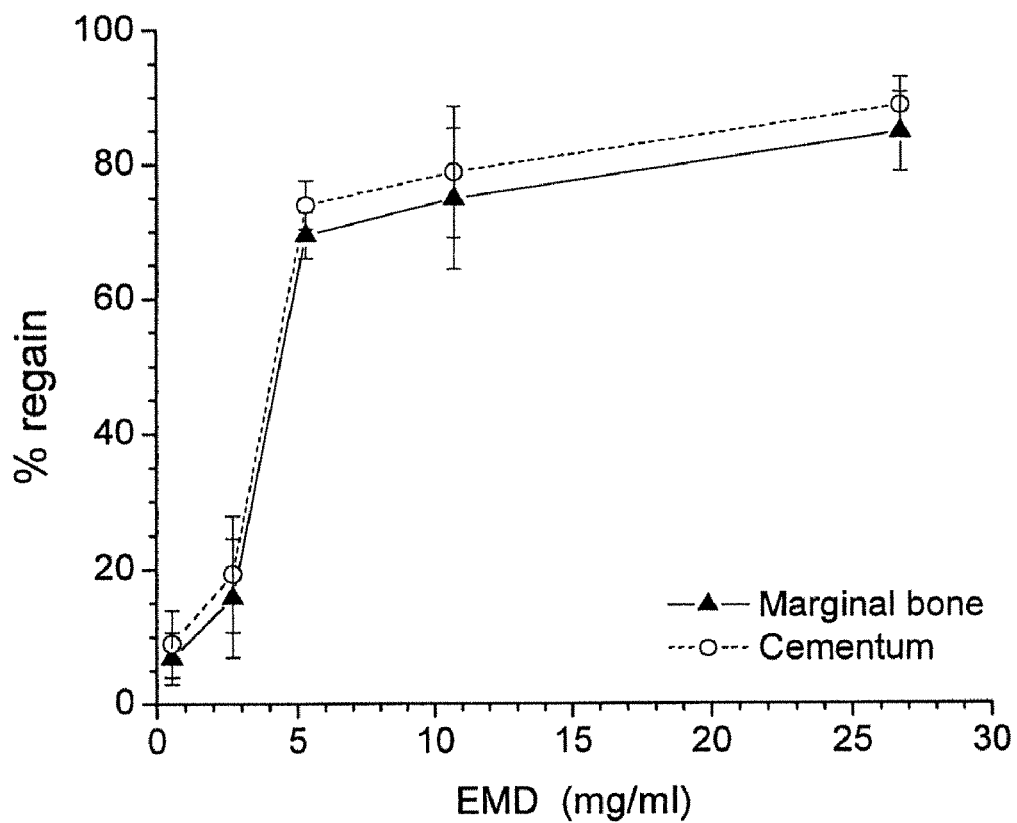
FIG. 1 shows regain of marginal bone and cementum versus concentration of EMD in the gel.

Evaluation: The tissue reactions on the exposed root surfaces were recorded and the distance, expressed in percent of exposed root surface, which had been covered by new alveolar bone and new cementum was measured (see FIG. 1).

Statistical methods: Non-parametrical statistical methods, i.e. Wilcoxon's Rank Sum Test and Mann-Whitney U Test, were employed to assess the significance of differences between test and control sites. The significance levels are denoted as follows:
1. NS not significant
2. * $p<0.05$
3. ** $p<0.01$
4. *** $p<0.001$ Storage of data and specimens; All raw data, specimens, the protocol and final report from this study are stored in the archives of BIORA AB, Krokusvägen 12, 181 31 Lidingö, SWEDEN. Relevant references: BIORA Scientific Report 9/88.

Results
Clinical observations: All animals remained healthy throughout the test period and no adverse side effects were noted. Healing in both test and control teeth was uneventful.
General behaviour: All animals behaved normally with no apparent differences between individual animals.
Food consumption: Food and water consumption appeared to be normal with no apparent differences between individual animals,
Terminal Studies:
Macroscopic examination: The gross appearance revealed healthy gingiva around all test teeth with no apparent gingival inflammation. No adverse side effects were noted. The buccal gingiva of all control teeth displayed a moderate inflammation with a reclined gingival margin.

Microscopic examination; Microscopic and morphometric examination revealed significant differences between the groups of test and control teeth (table 4 and 5).

New cementum, firmly attached to the instrumented root surface, had formed to varying degrees in the test teeth. The cementum layer contained functionally oriented periodontal fibres associated with a periodontal membrane as revealed by polarized light microscopy.

Furthermore, alveolar bone attached to the periodontal membrane was present to varying degrees on the exposed experimental root surfaces (table 4 and 5). The junctional epithelium had not proliferated further than the newly formed cementum layer and gingival inflammation was virtually absent.

Neither new alveolar bone nor any significant new cementum had formed in the control teeth. The originally exposed root surfaces were covered by a long junctional epithelium which had retracted to about half way down the root. A moderate gingival inflammation was present in the buccal oral mucosa.
Statistical analysis Differences between the groups of test and control teeth were found to be significant at various levels (tables 4 and 5).

Discussion

The aim of the present study was to assess the effect of different concentrations of Enamel Matrix Derivative admixed with the vehicle Propylene Glycol Alginate on regeneration of tooth supporting tissues, as well as to assess its biological safety. The model used in the present study is almost identical to the clinical settings intended for clinical use of Enamel Matrix Derivative. The test preparation was administered as a surgical aid during conventional periodontal surgery. The doses administered are both lower and higher, on a body weight basis, than the dose intended for use in humans, which is 7.5 mg protein in a single application of equivalent size. Sham operations were used as controls.

Tooth supporting tissues (cementum, periodontal membrane and alveolar bone) will not normally regenerate after treatment of marginal periodontitis. Instead, the exposed root surface will be covered by a layer of epithelial cells which does not provide a functional attachment for the root. Thus, tooth supporting tissues lost to periodontal disease can not be regenerated with conventional methods. This was confirmed by the results recorded for the control teeth. However, the root surfaces conditioned with the test preparations of 5.3, 10.7 and 26.7 mg protein/ml had developed an apparently new periodontal attachment apparatus.

Recent studies on the formation of the surface of the dental root have shown that it not only is covered with cementum but also with a thin layer of an enamel-like tissue. This enamel-like tissue is formed during development of the root prior to cementum formation. It appears to provide a suitable surface on which cells forming cementum can grow. Consequently, cementum is deposited on the enamel-like tissue and a proper attachment apparatus will develop.

The present study has shown that, by conditioning scraped (instrumented) root surfaces with doses of Enamel Matrix Derivative exceeding 10 mg, normal adhering cementum and associated periodontal membrane (functional periodontium) will form. Furthermore, alveolar bone associated with the periodontal membrane had formed. These structures are not normally formed after conventional periodontal surgery. Instead, epithelium from the gingiva will cover the exposed root surface and the marginal bone level will, at best, remain the same. This highlights the need for a new definition of successful periodontal regeneration, based on the findings of the present study.

Successful periodontal regeneration must involve formation of new cementum firmly attached to the instrumented root surface. The cementum layer must contain functionally oriented periodontal fibres associated with a periodontal membrane. Furthermore, newly formed alveolar bone attached to the periodontal membrane must be present.

It was also evident, that regain of new attachment and associated alveolar bone occurs only to the level of root surface covered by repositioned oral soft tissue. The higher up in a coronal direction that the root surface is covered, the higher the marginal bone gain is possible. Furthermore, it can be concluded from the results that a concentration of enamel matrix derivative solved in PGA, which is below 5 mg protein/ml is not sufficient for inducing successful periodontal regeneration. However, above this concentration, a sufficient coverage of the root surfaces appeared to be possible.

TABLE 4

Experimental outline and regain of cementum and alveolar bone. Expressed in percent (%) of the original level

| Monkey | Tooth | Treatment and protein concentration (mg/ml) | Regain of marginal bone (%) | Regain of cementum (%) |
|---|---|---|---|---|
| 11/87 | 14 | Control | 0 | 0 |
| 11/87 | 15 | Control | 0 | 1 |
| 11/87 | 24 | Control | 0 | 0 |
| 11/87 | 25 | Control | 0 | 2 |
| 12/87 | 14 | Control | 0 | 2 |
| 12/87 | 15 | Control | 0 | 0 |
| 12/87 | 24 | Control | 0 | 1 |
| 12/87 | 25 | Control | 0 | 3 |
| 16/88 | 14 | PEU 0.53 | 5 | 8 |
| 16/88 | 15 | PEU 0.53 | 12 | 16 |
| 16/88 | 24 | PEU 5.3 | 71 | 76 |
| 16/88 | 25 | PEU 5.3 | 65 | 69 |
| 17/88 | 14 | PEU 2.7 | 27 | 30 |
| 17/88 | 15 | PEU 2.7 | 13 | 19 |
| 17/88 | 24 | PEU 26.7 | 78 | 86 |
| 17/88 | 25 | PEU 26.7 | 83 | 85 |
| 18/88 | 14 | PEU 10.7 | 68 | 75 |
| 18/88 | 15 | PEU 10.7 | 84 | 87 |
| 18/88 | 24 | PEU 0.53 | 7 | 8 |
| 18/88 | 25 | PEU 0.53 | 3 | 4 |
| 19/88 | 14 | PEU 2.7 | 17 | 19 |
| 19/88 | 15 | PEU 2.7 | 6 | 9 |
| 19/88 | 24 | PEU 5.3 | 69 | 74 |
| 19/88 | 25 | PEU 5.3 | 73 | 77 |
| 20/88 | 14 | PEU 26.7 | 87 | 91 |
| 20/88 | 15 | PEU 26.7 | 92 | 94 |
| 20/88 | 24 | PEU 10.7 | 64 | 67 |
| 20/88 | 25 | PEU 10.7 | 84 | 87 |

TABLE 5

Statistical comparison between control and experimental groups

Test groups
Number of test sites: Twenty (20)
Table 5A
Mean regain of marginal bone:

| PEU 0.53 | PEU 2.7 | PEU 5.3 | PEU 10.7 | PEU 26.7 |
|---|---|---|---|---|
| 6.8% | 15.8% | 69.5% | 75.0% | 85.0% |

Table 5B
Mean regain of cementum:

| PEU 0.53 | PEU 2.7 | PEU 5.3 | PEU 10.7 | PEU 26.7 |
|---|---|---|---|---|
| 9.0% | 19.3% | 74.0% | 79.0% | 89.0% |

Control group
Number of control sites: Eight (8)
Mean gain of marginal bone: 0.0%
Mean gain of cementum: 1.1%
Statistical significance test
A non-parametrical statistical method, Mann-Whitney U Test, was employed to assess the significance of differences between test and control sites. The significance levels when comparing test and control groups for both regain of cementum and marginal bone were found to be:

Table 5C
Statistical significance

|  | PEU 0.53 | PEU 2.7 | PEO 5.3 | PEU 10.7 | PEU 26.7 | Control |
|---|---|---|---|---|---|---|
| PEU 0.53 | NS | NS | ** | *** | *** | NS |
| PEU 27 | NS | NS | * | ** | * | NS |
| PEU 53 | ** | * | NS | NS | * | ** |
| PEU 10.7 | *** | ** | NS | NS | NS | *** |
| PEU 26.7 | *** | * | * | NS | NS | *** |
| Control | NS | NS | ** | *** | *** | NS |

Example 2

Rat Critical Size Cranial Defect

Rat Cranial Surgery

This animal experiment protocol has been evaluated and permitted by the Veterinary Authority of the Canton of Zurich according to Swiss Federal law (Nr. 152/1997). Sprague-Dawley albino rats are used (84-92 days old, all female). They are housed in groups of four animals or less and kept on a standard diet.

27 animals are anesthetized by induction and maintenance with Halothan/$O_2$. The surgical area is clipped and prepared with Betadine for aseptic surgery. A linear incision is made from the nasal bone to the midsagital crest. The soft tissue is reflected and the periosteum is dissected from the site (occipital, frontal, and parietal bones). An 8 mm craniotomy defect is created with a trephine in a dental handpiece, carefully avoiding perforation of the dura. The surgical area is then flushed with saline to remove bone debris and a preformed gel is placed within the defect. The soft tissues are then closed with skin staples. After the operation, analgesia is provided by subcutaneous injection of Buprenorphine (0.1 mg/kg). Rats are subsequently sacrificed by $CO_2$ asphyxiation at the appropriate time after implantation. Craniotomy sites with 5 mm contiguous bone are recovered from the skull and placed in 40% ethanol, or placed in fixation medium (paraformaldehyde 4%).

At all steps, the surgeon is blinded regarding the treatment of the defects.

Preparation of Gels

EMD was dissolved in 0.10% acetic acid to yield stock solutions with various concentrations, depending on the desired EMD content of the final gels. Cystein-RGD, PEG-dithiol 3.4 k, and 4-arm PEG-acrylate 15 k were dissolved in 0.30 M triethanolamine/HCl buffer, pH 8.5. PEG-EMD gels were cast by mixing all solutions to yield 20 µl solution containing ca. 15 wt % PEG with equimolar numbers of acrylate and thiol groups, 8 µg cystein-RGD and 0-250 µg EMD. The solution was allowed to gel for 1 hr at 37° C. and the gels were then transferred to PBS, pH 7.4. After a few hours they had swollen to a volume of 100 µl, and a diameter of 8 mm.

Radiography

Figure 2:
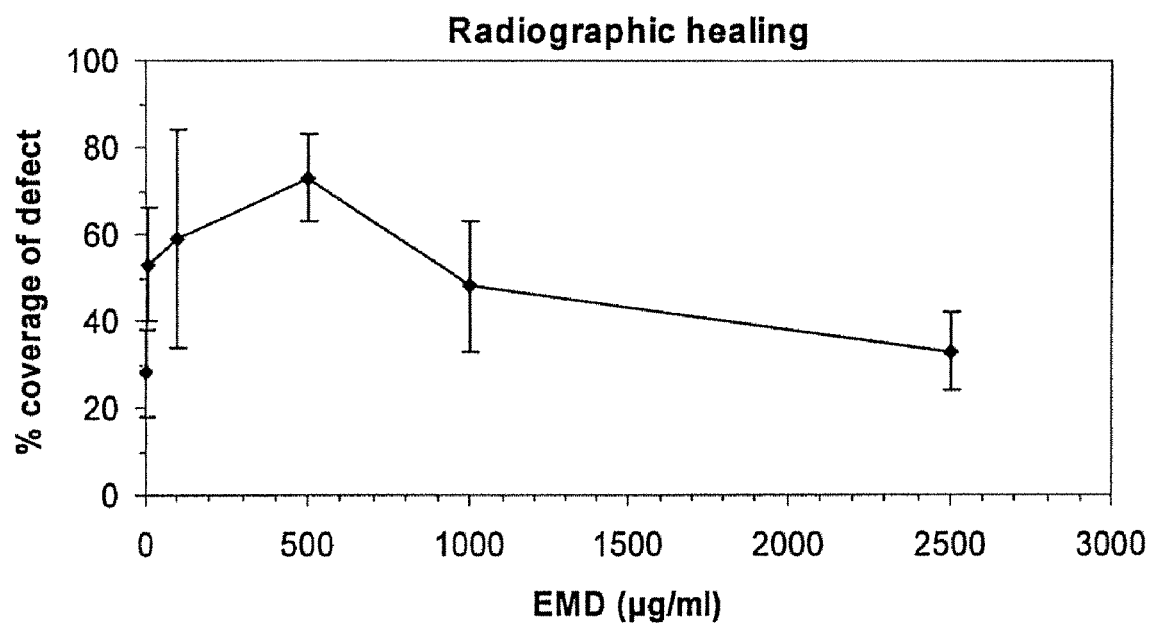
FIG. 2 shows healing of critical size bone defects in the rat skull as a function of the concentration of EMD in the inserted gel (n=4-5)

Specimens obtained after sacrifice and removal of the defect site with the surrounding 5 mm contiguous bone are imaged using a dental radiography unit with ultra speed dental films (Eastman Kodak Company, NY, USA) The radiographs are then scanned and the digital images processed with an image analysis program (Leica® Q-Win). The area of new bone formed inside and outside the defects is calculated as percent of the original defect area to compare the healing rate of the different formulations (see FIG. 2).

Example 3

Tooth Supporting Tissue Regeneration in Pig

Aim:

To use a dehiscence model for clinical, quantitative and histological comparisons of the local effects of treatment with enamel matrix derivatives and/or graft materials, PEG gels and on healing and regenerative processes in the jaw as compared with sham control teeth.

Animals:

Minipigs, *Sus scrofa*, adults (>18 months), females. The animals are acclimatized and observed in the local animal facilities prior to surgery.

Experimental Description:

1. The animal is maintained under anesthesia (i.m. Ketalar+i.v. Pentotal and Dormicum). Local anesthesia with Xylocain-adrenalin (Dental).
2. The animal is inspected
3. If necessary, the pig is shaved around the mouth and the skin is then rinsed with Chlorhexidin® (5 mg/ml in 60% EtOH). The operation area is photographed.
4. Start in Q1: Infiltration anesthesia is applied in the mucobuccal fold. Injections into the interdental papilla and marginal gingival area are to be avoided.
5. The degree of inflammation is evaluated and plaque and calculus removed.
6. A marginal incision is made from the first premolar to the first molar with perpendicular releasing incisions at the ends. The mucoperiosteal flap is raised to expose the alveolar bone.
7. The buccal bone is carefully removed, using a burr and manual instruments, from each tooth root creating dehiscence defects about 6 mm deep and 2 mm wide. From the exposed root surface the periodontal ligament and cementum are removed, under constant irrigation with sterile saline, from the second premolar to the fourth premolar to a distance of 6 mm from the CEJ. The apical end of the defect (AED) is marked with a notch. A total of 6 defects are to be created in each quadrant (i.e. 12 in each jaw/animal).
8. After removal of the ligament and cementum, the tooth surfaces are treated with PrefGel® (BIORA, Sweden) for 2 minutes before being washed with ample amounts of sterile saline.
9. The distance from CEJ to the AED is measured and noted and documented by photography.
10. The test material (See treatment list, sham=none) is applied in the defects and documented by photography.
11. The flap is immediately repositioned and closed with vicryl sutures. The flap completely covers the bone defects and the flap is thoroughly repositioned and fixed, which is again documented by photography.
12. According to items 4-14 the procedure is repeated for Q2.

Post Treatment:

The animals are put on soft diet for 1 week after surgery. Antibiotic (Streptocillin 5 mill u/day is administered for 2 days from surgery. Analgesics (Voltaren, 25 mg after surgery).

Observation

At 4, 6 and 8 weeks the animals are sedated and the healing of the experimental defects are inspected. The defects depths are probed using a standard pocket probe (human clinic) and the "pocket probing depth" is recorded in millimetres for each defect together with the extent (if any) of gingival recession. The healing is documented by photography. All adverse events are noted.

Termination:

The experiment is terminated and the animals are sacrificed after 8 weeks of observation:

1. 40 ml Pentobarbital natrium 100 mg/ml in Spiritus fort. 290 g/1000 ml is given i.c. to animals 8 weeks after surgery according to the test scheme.
2. A segment including all experimental teeth with complete roots are cut out from each experimental jaw.

3. The separate segments are immediately submerged in a large volume (200 ml) freshly prepared, refrigerated (4° C.), phosphate buffered formalin Ph 7.4. The containers must be carefully labelled with animal number, quadrant number, surgeon and date. The formalin is changed once after 4 hours to ensure good fixation.
4. The samples are processed for embedding in epoxy and sectioning by grinding as soon as possible. Until processing is possible the formalin fixed samples are stored in the refrigerator.

Preparation of Kits

All materials are handled under aseptic conditions.

PEG-Thiol/EMD Solution:

1.20 g of 4-arm PEG-thiol 2 k (Nektar) was dissolved in 20 ml of sterile 0.05% aqueous acetic acid solution. This solution was sterilized by filtration. 0.520 g of sterile EMD was dissolved in 10 ml of sterile 0.05% aqueous acetic acid solution. Both solutions were combined and sterile glass syringes were filled with each 300 µl of the PEG-thiol/EMD solution. (12 mg of 4-arm PEG-thiol 2 k and 5.2 mg of EMD per syringe)

Activator Solutions:

1.865 g of triethanolamine (Merck, PhEur) was dissolved in 250 ml of WFI (0.050 M) and the pH of the solution was adjusted to pH 8.6 using HCl.

5.0 g of Keltone HVCR (ISP) was dissolved in 95 ml of the triethanolamine/HCl solution under vigorous stirring. The resulting solution was filled into plastic syringes with a female luer (678 mg). 3.0 g Cekol 10'000 (Noviant; 51408) was dissolved in 80 ml of the triethanolamine/HCl solution under vigorous stirring. The resulting solution was filled into plastic syringes with a female luer (678 mg). The activator syringes were placed individually in peel bags and steam sterilized (121° C./15 min).

PEG-Acrylate Vials:

3.6 g of 4-arm PEG-acrylate 15 k (Nektar) were dissolved in 35 ml of WFI. In a clean room, 0.70 ml aliquots of this solution vials were filled into vials and lyophilized. After lyophilization, the vials were filled with nitrogen and closed. (72 mg of 4-arm PEG-acrylate 15 k per vial)

Preparation of the PEG/EMD Gels (4.9 mg EMD Per g Gel): Just before application, the lyophilized PEG-acrylate was reconstituted in the PEG-thiol/EMD solution and the resulting solution was transferred back to the glass syringe, which was then coupled to an activator syringe. The contents of both syringes were mixed by moving the plungers back and forth ca. 15 times. After mixing, the product could be applied for ca. 2 min, before it had completely gelled.

All defects were treated with PrefGel® in 1 minute followed by ample rinsing with saline prior to application of test article.

List of Articles Used:

| PrefGel | Lot 1008 |
|---|---|
| Emdogain 30 mg/ml | Lot ETP 3102 |
| PGA | Lot FoU 2113 in 1.5 ml vials |
| EMD 9.5 mg/vial | Lot 9102 |
| Bone Ceramic | Lot LK 040109 |

Results

Figure 3:
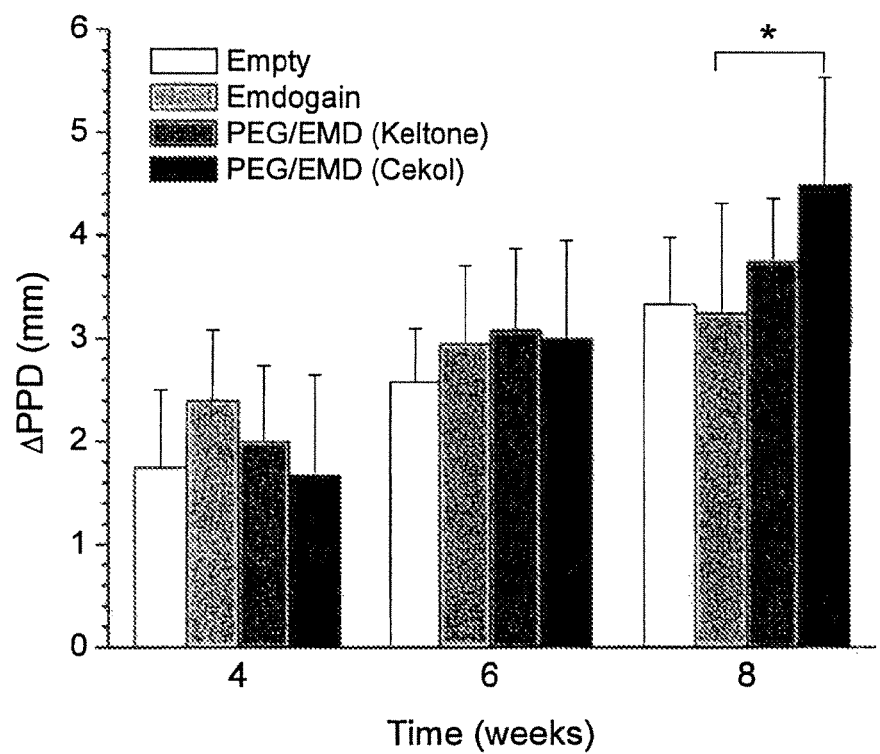
FIG. 3 shows pocket depth measured from the CEJ to the Apical end of the defect in millimeters, where * P<0.05 (one-way ANOVA test with Bonferroni adjustment)

As can clearly be seen in table 7, active enamel substance derivative (EMD) at a concentration of 4.9 mg/ml in GLP 41/47 did have a similar, or even a more pronounced effect on the healing of the experimental defects than Emdogain 30 mg/ml. The results are summarized in FIG. 3. Also, as can be deducted in FIG. 3, comparing empty, Emdogain and EMD at a concentration of 4.9 mg/ml in either Keltone or Celco gels, after 4 weeks Emdogain performs somewhat better than EMD at a concentration of 4.9 mg/ml in either Keltone or Celco gels, after 6 weeks they perform roughly equally and after 8 weeks EMD at a concentration of 4.9 mg/ml in either Keltone or Celco gels performs better. This corresponds very well with the degradation time of 4 weeks found for this type of gel in vitro (37° C., pH 7.4). As long as the PEG gel is present one would expect it to hinder filling of the defect with bone to a certain degree.

TABLE 7

Pocket probing depth in mm: Difference in mean between surgery and observation time points.

| Pig expnr | Q1 w 4 | Q1 w 6 | Q1 w 8 | Q2 w 4 | Q2 w 6 | Q2 w 8 |
|---|---|---|---|---|---|---|
| 1 | 1.7 | 2.7 | 3.2 | 1.8 | 2.5 | 3.5 |
| 2 | 2.5 | 3.2 | 3.5 | 2.7 | 2.5 | 2.7 |
| 3 | 2.5 | 3.0 | 3.5 | 1.8 | 3.3 | 3.5 |
| 13 | 1.7 | 2.5 | 3.5 | 2.3 | 3.7 | 4.0 |
| 14 | 1.3 | 3.0 | 4.5 | 2.0 | 3.0 | — |

TABLE 6

Experimental set-up of minipig surgery

| EXP nr | PIG ID | TREATMENT planned | TREATMENT performed |
|---|---|---|---|
| 1 | 62307 | Q1: Sham surgery | Q1: Sham |
|  |  | Q2: Sham surgery | Q2: Sham |
| 2 | 65867 | Q1: Emdogain 30 mg/ml | Q1: Emdogain 30 mg/ml |
|  |  | Q2: Emdogain 30 mg/ml | Q2: Emdogain 30 mg/ml |
| 3 | 64447 | Q1: Emdogain 30 mg/ml | Q1: Emdogain 30 mg/ml |
|  |  | Q2: Emdogain 30 mg/ml | Q2: Emdogain 30 mg/ml |
| 13 | 66770 | Q1: EMD 5 mg/ml + EMD 2nd gener. ALG | Q1: Keltone-buffer, GLP 41/46 + Emdogain 5 mg/ml, GLP 41/47 |
|  |  | Q2: EMD 5 mg/ml + EMD 2nd gener. ALG | Q2: Keltone-buffer, GLP 41/46 + Emdogain 5 mg/ml, GLP 41/47 |
| 14 | 82118 | Q1: EMD 5 mg/ml + EMD $2^{nd}$ gener. CMC | Q1: Cekol-buffer, GLP 41/45 + Emdogain 5 mg/ml GLP 41/47 |
|  |  | Q2: EMD 5 mg/ml + EMD $2^{nd}$ gener. CMC | Q2: Cekol-buffer, GLP 41/45 + Emdogain 5 mg/ml GLP 41/47 |

Example 4

Rabbit Cranial Cylindrical Drill Defect

The results of this experiment provides information regarding the effect of a new bioactive bone substitute on guided bone regeneration.

Hypothesis:

The effect of binding active enamel substances to a newly developed matrix with optimized cell ingrowth capabilities enhances bone tissue regeneration comparing to standard grafting procedures (positive control) and to spontaneous healing (negative control)

Materials and Methods:

Animals 24 adult New Zealand White rabbits, weighing between 3 and 4 kg, were used in the present study. The animals were kept in a purpose-designed room for experimental animals and were fed with standard laboratory diet.

Surgical Procedures and Materials:

A straight incision was made over the fore-head (calvaria) of 24 New Zealand White rabbits and two cutaneous flaps were raised and reflected laterally. Similarly, the periosteum was cut and reflected exposing the top of the cranial bone. In the area of the right and left parietal and frontal bones, a circular groove was prepared using a trephine drill with a sleeve that only allows for a 1 mm drill depth. Care was taken to make sure that the external cortical plate inside this circle was not removed. Five small round drill defects were made in the top cortical plate inside the circle to allow better access to bone marrow in the chamber. Subsequently, a cylindrical tube made of titanium with a 1 mm deep threaded notch was seated in each of the grooves for primary stability. The 4 tubes exhibited a machined surface on their inside. The tubes measured 6 mm in height and 6 mm in outer diameter.

The distribution of materials depended on each individual study. However, in each study, one of the tubes served as a negative control and was left empty. The next three materials included the test materials as well as a positive control if appropriate. When the positive control was used, a standard grafting material was employed. One option was using a bovine-derived bone mineral used today in standard human grafting procedures (Bio-Oss®, Geistlich A G, Wolhusen, Switzerland). The materials were distributed amongst the cylinders in each animal, such that the number of cylinders anterior and posterior for each animal were the same and the number on the left and the right were the same. Finally, to control for systemic effects, if a dosing series was performed, no two materials with different doses of active factor were placed in the same animal and some control samples were purposely placed in animals which never received active enamel substance treatment. Each sample was made in pairs in an individual animal so identical materials in the front and back were a set.

The tubes were left open towards the bone side but were closed with a titanium lid towards the covering skin-periosteal flap. The periosteum and the cutaneous flap were adapted and sutured. 4, 8 and 16 weeks later, 8 animals were sacrificed. The number of samples at each time point for each treatment was eight.

Matrices and Growth Factors

Basically two different matrices were used in this trial. A fibrin matrix derived from human fibrinogen and a synthetic based PEG gel, both specifically modified for high cell ingrowth capabilities. The gels comprised a specific active enamel substance, whereby the active enamel substance interacted with its delivery matrix (covalent bonding) to achieve a specific release profile after implantation. The gels were alternatively mixed with synthetic calcium phosphate granules. The used granules consisted of a mixture of a porous tricalciumphosphate/hydroxyapaptide (ratio 40:60) that is widely used in human surgery, to achieve a putty-like reconstruction material for grafting procedures.

EMD was prepared in two concentrations and in two gel types:

PEG+100 µg/ml EMD and PEG+500 µg/ml EMD data and PEG/RGD+500 µg/ml EMD

Histologic Preparation and Histomorphometry

The specimens were processed according to standard procedures for ground sections without decalcification. The bone density within the tube and along the walls of the tube was quantitatively assessed applying standard histomorphometrical techniques Statistics The one-way ANOVA test with Bonferroni adjustment was used to detect differences between test and control, as well as over time with respect to test or control. The level of significance in all statistical tests is chosen at $\alpha=0.05$.

Results

Figure 4:
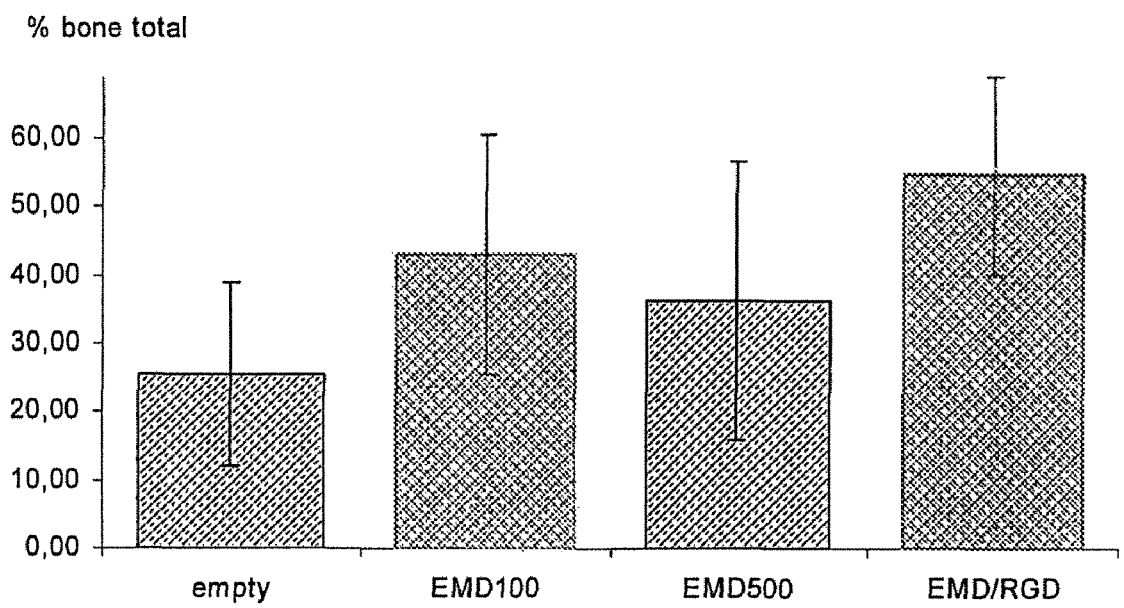
FIG. 4 shows the bone density within the tube and along the walls of the tube as quantitatively assessed applying standard histomorphometrical techniques.
Figure 5:
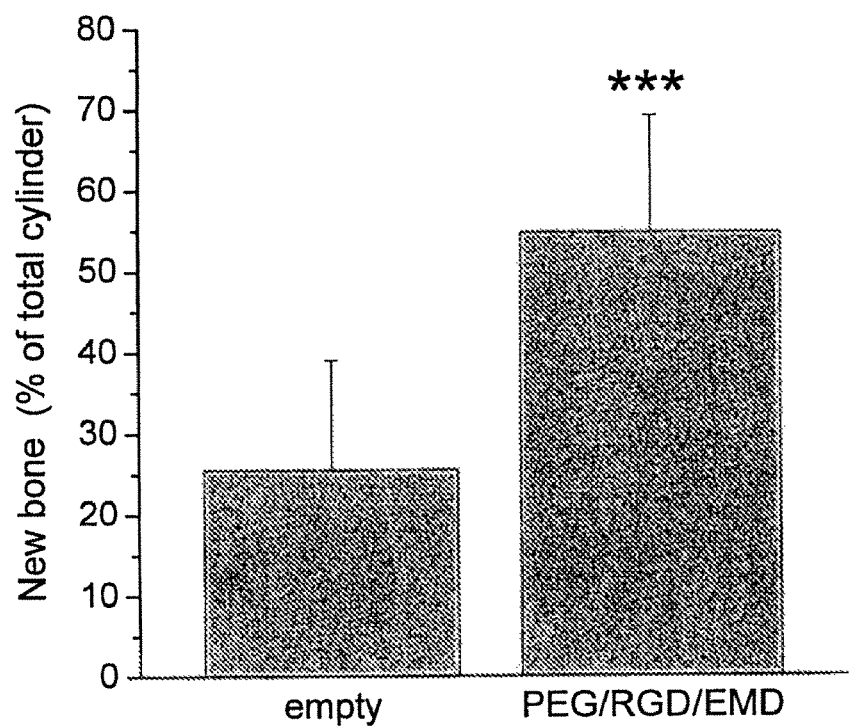
FIG. 5 shows the bone density within the tube and along the walls of the tube as quantitatively assessed applying standard histomorphometrical techniques, where *** P<0.001 (one-way ANOVA test with Bonferroni adjustment)

FIGS. 4 and 5, clearly demonstrate that PEG/RGD+500 µg/ml EMD has the best effect on bone regrowth. Thus binding active enamel substances to a newly developed matrix with optimized cell ingrowth capabilities enhances bone tissue regeneration.

Example 5

Periodontal Dehiscence Model in Mini-Pigs

1. Introduction and Rationale

Enamel Matrix Derivative (EMD) prepared with two new carriers (PEG with alginate or CarboxyMethylCellulose) has been tested in the present Investigation.

The mini-pig dehiscence model is of historical reference when it comes to clinical, quantitative and histological comparisons of the local effects of treatment with Enamel Matrix Derivatives (EMD) on healing and regenerative processes of periodontal tissues.

3. Objectives

The main objective to be followed consisted in the evaluation of the periodontal regeneration comparatively between Emdogain® and Enamel Matrix Derivative (EMD) prepared with two new carriers (PEG with alginate or CarboxyMethylCellulose).

4. Variables Under Investigation 4.1. Primary Variable

The primary variable consisted in the clinical evaluation of the reduction in periodontal pocket probing depth.

4.2. Secondary Variables

The descriptive histology and the histomorphometry based on evaluation of the reduction of bone defect depth, cement height, periodontal ligament presence, bone area formed the first group of secondary variables.

When it comes to quantitative evaluation of mineralized tissues, bone measurements on microXrays greatly improved the quality of the histomorphometrical approach as only mineralized tissues appear on the sections. It is the reason why in this study the histomorphometry has been conducted on microXrays obtained from histological sections.

The inflammation grade (no, mild, moderate, severe), the length and width of the recession (measured in mm from the Cementum-Enamel Junction to the top of the gingiva) belonged to the second group of secondary variables.

5. Materials and Methods 5.1. Animals

Minipigs, *Sus scrofa*, adults (>18 months), females. The animals have been acclimatized and observed in the local animal facilities prior to surgery.

5.2. Surgery and Post-Surgery 5.2.1. Surgery

The animals have been maintained under general anesthesia (i.m. Ketalar+i.v. Dormicum). Furthermore local anesthesia with Xylocain-adrenalin was performed locally.

The different steps of the procedure were the following:

Inspection of the animal and record in page 1 of the Record Form.

The pigs were shaved around the mouth and the skin was then rinsed with Chlorhexidin® (5 mg/ml in 60% EtOH).

Start in Q1: Infiltration anesthesia in the mucobuccal fold was performed by avoiding injections into the interdental papilla and marginal gingival area.

The degree of inflammation has been evaluated and the plaque and calculus removed.

After a marginal incision from the first premolar to the first molar with perpendicular releasing incisions at the ends has been made, the mucoperiosteal flap was raised in order to expose the alveolar bone in the upper jaws.

By help of burr and manual instruments "windows" of buccal bone plate as well as periodontal ligament and cementum have been removed from the second premolar to the fourth premolar under constant irrigation with sterile saline. The vertical defects have been created in the main axis of each teeth root to a distance of 5-6 mm from the CEJ. The apical end of the defect (AED) was marked with a notch.

The mean final dimensions of the defects were the following: height=6 mm, width=2 mm, depth=3 mm.

After removal of the ligament and cementum, the tooth surfaces were treated with PrefGel for 2 minutes before being washed with ample amounts of sterile saline.

The distance from CEJ to the AED was measured and recorded.

The test materials (sham=none) have been applied into the defects.

After the repositioning of the flap, the operation site was closed with vicryl sutures. It was pay a particular attention to get sure that the flap completely covered the bone defects and that it was thoroughly repositioned and fixed.

The same procedure was repeated for the second quadrant.

Figure 6:
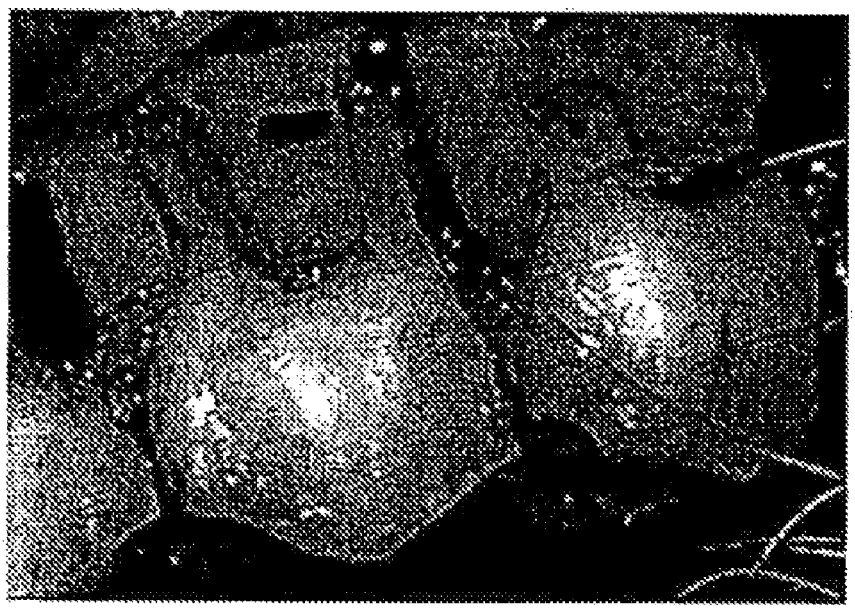
FIG. 6 shows a periodontal dehiscence model in mini-pigs, surgery set-up.

FIG. 6 shows a typical surgery wound.

5.2.2. Post-Surgery

The animals have been put on soft diet for 1 week after surgery. Antibiotic (Streptocillin 5 mill u/day was administered for 2 days from surgery, analgesics (Voltaren, 25 mg) after surgery.

5.3. Groups in Test and Controls

A total of 10 animals was included in this study but one died for reasons not related to the implantation of one of the tested materials.

As two defects were prepared on each maxilla tooth and 6 teeth used in each animal the total number of defects in each animal was 12.

In the more relevant groups (see below) a total of 48 defects have been evaluated for each type of treatment.

The following groups were under investigation:

5.3.1. Test Groups

PEG-Ec=PEG (with CMC)+EMD (at a concentration of 4.9 mg/ml): 4 animals

PEG-Ek=PEG (with Alg)+EMD (at a concentration of 4.9 mg/ml): 3 animals 5.3.2. Positive Control Group Emdogain® (commercially available, with EMD at a concentration of 30 mg/ml): 1 animal 5.3.3. Negative Control Group

TABLE 7

Empty: 1 animal

|  | Number of animals |
|---|---|
| Sham | 1 |
| Emdogain | 1 |
| PEG-Ek (Alg) | 3 |
| PEG-Ec (CMC) | 4 |

5.4. Healing Time

According to the previous data available at Straumann-Biora (Malmö) it was foreseen to assess the clinical situation and to perform periodontal measurements after 4, 6 and 8 weeks. Furthermore histological evaluation (qualitative and quantitative) has been conducted after an 8 week healing period.

5.5. Termination

An injection of 40 ml Pentobarbital natrium 100 mg/ml in Spiritus fort. 290 g/1000 ml was given i.c. to the animals 8 weeks after surgery according to the test scheme.

A segment including all experimental teeth with complete roots were cut out from each experimental upper jaw.

5.6. Time Schedule 5.7. Methods of Analysis 5.7.1. Periodontal Probing

The periodontal probing performed with a probe was intended to evaluate the pocket depth at operation day and after 4, 6 and 8 weeks. These measurements were done in accordance with the classical rules of the "blind method". The investigator did not know to which group belonged the animal under examination.

5.7.2. Histology

The separate segments were immediately submergery in a large volume (200 ml) freshly prepared, refrigerated (4° C.), phosphate buffered formalin Ph 7.4. The formalin was changed once after 4 hours to ensure good fixation.

The samples were processed for embedding in epoxy and sectioning by grinding (to a thickness of about 25 μm).

Samples were processed by classical non-demineralized preparation methods followed by embedding in methyl methacrylate, sectioning (Polycut-S, Reichert-Jung, Leica Microsystems Switzerland) and staining with toluidine blue.

The histology sections have been used for the qualitative and semi-quantitative analysis which intended to define the presence of a periodontal ligament in the grafted site.

5.7.3. Micro-Radiography

Using an X-rays generator, micro-radiographies were performed on histological sections before the final grinding has been attempted (thickness 50 μm) and quantitatively analysed under light microscopy to evaluate the height and area of bone.

6. Results
6.1. Clinical Periodontal Probing and Recession Measurements

Only the results related to pocket depth measurements will be summarized herein.

6.1.1. Clinical Periodontal Probing

These clinical measurements demonstrated that each treatment by itself is beneficial in terms of pocket depth reduction. It exists a progressive decrease of the pocket depth inside each group from day of operation to week 8, through weeks 6 and 4. The differences are statistically significant inside each group between these different time-points. The only exception is the presence of a plateau phase from week 4 to week 8 for the Emdogain group.

In some cases differences are also statistically significant when comparing the respective time-points from one group to another.

TABLE 8

| Treatment | Number of defects (n) | Pocket depth at op | Pocket depth after 4 weeks | Pockets depth after 6 weeks | Pockets depths after 8 weeks |
|---|---|---|---|---|---|
| PEG/Ec | 47 | 6.69 | 4.74 | 3.98 | 3.28 |
| PEG/Ek | 35 | 6.68 | 5.18 | 3.47 | 3.48 |
| Emdogain | 12 | 6.35 | 3.60 | 3.65 | 2.45 |
| Sham surgery | 12 | 6.65 | 5.05 | 2.65 | 2.25 |

6.2. Histology (Qualitative and Semi-Quantitative Analysis)

Qualitatively the Emdogain® group showed the regeneration of a mature and lamellar bone separated from the new cement by a well organized periodontal ligament.

In general the PEG-Ek and PEG-Ec groups demonstrated the presence of a non-mature and densely vascularized new bone which seemed to keep the place where the 2 PEG matrices had been positioned during the surgery (see FIGS. 7 and 8).

It was observed that in the case of PEG-Ec (CMC) the periodontal ligament presence was equivalent to those found in the Emdogain® group (see FIGS. 9 and 10).

The doubtful cases have not been taken into account in the following table:

TABLE 9

| | Number of defects (n) | Periodontal ligament | Percentage of presence |
|---|---|---|---|
| Sham | 12 | 4 | 33% |
| Emdogain | 12 | 8 | 66% |
| PEG-Ek (Alg) | 36 | 17 | 47% |
| PEG-Ec (CMC) | 48 | 33 | 68% |

Amount of doubtful cases in terms of periodontal ligament presence assessment:

| | |
|---|---|
| Sham = 5 | PEG-Ek = 9 |
| Emdogain = 4 | PEG-Ec = 10 |

6.3. MicroXrays (Quantitative Analysis)
Bone Height

All the groups experienced a significant bone gain of at least 2 mm. Emdogain® reached the highest performance (about 4 mm) with a statistical significance comparatively to the 2 EmdogainGeneration2 groups ($p<0.005$).

The sham group performed less well than Emdogain® but better than the PEG-Ec or PEG-Ek groups. See also FIG. 11.
Bone Area In the four groups a respectable amount of bone was regenerated (about 3 mm2) without any statistical difference between the four conditions.

TABLE 10

| | Number of defects (n) | Bone height gain (mm) | Area (mm2) |
|---|---|---|---|
| Sham | 6 | 2.87 (+/−1.51) | 2.54 (+/−1.1) |
| Emdogain | 8 | 3.85 (+/−0.84) | 2.99 (+/−1.36) |
| PEG-Ek (Alg) | 28 | 2.26 (+/−0.95) | 2.97 (+/−2.17) |
| PEG-Ec (CMC) | 30 | 2.28 (+/−0.89) | 3.28 (+/−2.21) |

7. Discussion

In terms of bone height Emdogain® performed accordingly to existing results and already published literature. The sham group showed better results than EmdogainGeneration2.

PEG-Ec showed a periodontal ligament presence equivalent to Emdogain® but only on a length which can approximatively be estimated to about 2 mm.

Although the morphologies of the regenerated bone structures were different between the two the PEG-Ec or PEG-Ek (see e.g. FIG. 12), it appeared that the use of PEG-Ec and PEG-Ek resulted in the formation of an amount of bone similar to those regenerated by Emdogain®. It is hypothesized that the regeneration of this newly formed bone took actually place inside the two PEG matrices supplemented with EMD. Then the volume and position of these matrices at implantation day could act upon the volume and the height of the corresponding bone regeneration.

Example 6

Evaluation of a New Active Enamel Derivative Formulation (PEG-EMD) for Periodontal Regeneration An Experimental Study in Class 3 Furcation Defects in Dogs

1. State of the Art and Rationale
The present study is intended to follow a pilot one ("Evaluation of Emdogain® Generation2: a pilot study in a periodontal dehiscence model in mini-pigs") where the following has been reported:

"Although the morphologies of the regenerated bone structures were different between the two types of Emdogain®Generation2 and Emdogain®, it appeared that the use of PEG-Ec and PEG-Ek (both called PEG-EMD) resulted in the formation of an amount of bone similar to those regenerated by Emdogain®.

It is hypothesized that the regeneration of this newly formed bone took actually place inside the two PEG matrices supplemented with EMD. Then the volume and position of these matrices at implantation day could act upon the volume and the height of the corresponding bone regeneration".

2. Hypothesis
PEG-EMD induces a periodontal regeneration (bone, ligament) which is not inferior to the periodontal regeneration obtained by the use of Emdogain® when applied in the treatment of furcation (class 3 Hamp) defects.

3. Objectives
3.1. Principal Objective
The main objective of this study shall be to demonstrate in a dog model that PEG-EMD induces quantitatively higher bone regeneration than Emdogain® when used for the treatment of class 3 furcation defects.
3.2. Supplementary Objectives
As a second objective it shall be shown that the regeneration of the periodontal ligament after application of PEG-EMD is not inferior to those obtained by using Emdogain® in the above cited model.
4. Variables
4.1. Primary Variable
The difference in new bone height built up between the baseline and the end-points and comparatively between test (PEG-EMD) and positive control (Emdogain®) groups.
4.2. Secondary Variable
The presence of a periodontal ligament lining the surface on at least one root surrounding the furcation.
4.3. Tertiary Variable
Qualitative data giving when put together a complete description of bone, periodontal ligament, cementum and soft tissues structures.
5. Animal Model and Management
5.1. Animal Model
Hound dogs, about 16 month old and weighting about 25 kgs
Extractions of P1 and M1, P2 and P3 will stay in place.
3 months later: creation of a furcation defect of 5 mm height on P2 and P3 (Koo et al., 2004). (See FIG. 13 for a typical surgical set-up. On the drawing each arrow corresponds to 5 mm.)
5.2. Animal Management
The animal housing, surgical procedures and follow-up will be conducted according to GLP rules at the following experimental surgery facilities:
BiomatechNAMSA, Chasse sur Rhone (Lyon), France.
6. Expected Results and Power Calculation
The literature reports that the mean height of the defect inside the class 3 furcation at base line is 4.7 mm (+/−0.2). It is expected that the spontaneous healing after 4 weeks results in a bone height gain of 1.8 mm (+/−0.3). (Koo et al., 2004) →negative control groups: blank and PEG
A similar result is expected after 4 weeks from the control group (Emdogain®). After 2 and 4 months the increase should remain limited, about 1.5 mm (+/−0.5)
The test group (PEG-EMD) should show a bone gain of 2.0 mm (+/−0.5) after 4 weeks, 2.5 mm (+/−0.5) after 2 months and 3.0 mm (+/−1.0) after 4 months.
7. Materials and Methods
7.1. Materials
7.1.1. Testmaterial
PEG-EMD:
Vial containing 72 mg of lyophylized 4-arm PEG-acrylate 15 k
Syringe containing 300 µl solution of 12 mg 4-arm PEG-thiol 2 k and 5.2 mg EMD in 0.05 wt % aqueous acetic acid.
Syringe containing 680±10 mg of 0.05 M aqueous triethanolamine/HCl,
pH 8.5±0.1 containing 3.6 wt % of Cekol 10'000
Final concentration of EMD in PEG: 4.9 mg/ml
7.1.2. Positive Control
Emdogain®
Concentration of EMD in PGA: 30 mg/ml
7.1.3. Negative Control
Empty
PEG
7.1.4. Complementary Material
No complementary material
7.2. Methods
7.2.1. Study design and schedule
t 0:
Extractions of P1 and M1
t 3 months: grinding of alveolar ridge, creation of class 3 furcation defect on P2 and P3
t 4 months: sacrifice after 1 month observation time
t 5 months: sacrifice after 2 months observation time
t 7 months: sacrifice after 4 months observation time
7.2.2. Pre-Surgical Phase
Extraction of teeth,
Healing time: 3 months
7.2.3. Surgical Phase
Creation of two class 3 furcation defects on each mandibular side per animal.
Filling of furcation defect with test or control material.
Suturing is critical
7.2.4. Post-Surgical Phase
Remove of sutures after 14 days of healing.
6 weeks following surgery, postoperative plaque control.
7.2.5. Observations and Analysis
Micro-computed tomography, histology and histomorphometry
8. End-Points and Terminal Procedure
Animals will be sacrificed at 1, 2 and 4 months after surgery.

LIST OF REFERENCES

1. Altschul, S. F. et al (1990)
2. Aoki, et al., Thrombosis and Haemostasis, 39:22-31, 1978
3. Aoki, N., Progress in Cardiovascular Disease, 21:267-286, 1979
4. Besson et al., (1996) Anal. Biochem. 237:216-223
5. Carey, Annual Review of Physiology, 53:161-177, 1991
6. Coombs et al., (1998) J. Biol. Chem. 273-4323-4328
7. Devereux, J et al (1994)
8. Edelman et al. (Biomaterials 1991 September; 12(7):619-26)
9. EP-B-0 263 086
10. EP-B-0 337 967
11. EP-1059934
12. EP-01201915.4
13. Francis, et al., Blood Cells, 19:291-307, 1993
14. Gestrelius S, Lyngstadaas S P, Hammarstrøm L. Emdogain—periodontal regeneration based on biomimicry. Clin Oral Invest 4:120-125 (2000).
15. Graf, et al., Cell, 48:989-996, 1987;
16. Hammarström et al., 1997, Journal of Clinical Periodontology 24, 658-668).
17. Hata, et al., J. Biol. Chem. 268: 8447-8457
18. Haugen, et al., (1992). J. Neurosci. 12: 2034-2042
19. Hem et al., J. Biomed. Mater. Res. 39:266-276 (1998)
20. Ignatius, et al., J. of Cell Biology, 111:709-720, 1990
21. Kallapur, et al, Adhesion Molecule (1992) J. Neurosci. Res. 33: 538-548
22. Kleinman, et al., Archives of Biochemistry and Biophysics, 272:39-45, 1989
23. Liesi, et al., FEBS Letters, 244:141-148, 1989
24. Lyngstadaas et al., 2001, Journal of Clinical Periodontology 28, 181-188
25. Lyngstadaas et al., 2000, Journal of Clinical Periodontology 27, 1-8
26. Martin, Annual Review of Cellular Biology, 3:57-85, 1987
27. Massia, et al, J. of Biol. Chem., 268:8053-8059, 1993

28. Netzel-Amett et al., (1991) J. Biol. Chem., 266:6747-6755
29. Sakata, et al., Journal of Clinical Investigation, 65:290-297, 1980
30. Sambrook, J. et al.: Molecular Cloning, Cold Spring Harbor Laboratory Press, 1989.
31. Schense, J. C., et al. (1999) Bioconj. Chem. 10:75-81
32. Sierra, D. H., Journal of Biomaterials Applications, 7:309-352 (1993)
33. Smith et al., (1995). J. Biol. Chem. 270:6440-6449
34. Stryer, L. In Biochemistry, W. H. Freeman & Company, NY, 1975
35. Takagi and Doolittle (1975) Biochem. 14:5149-5156
36. Tashiro, et al., J. of Biol. Chem., 264:16174-16182, 1989
37. Ten Cate: Oral Histology, 1994; Robinson: Eur. J. Oral Science, January 1998, 106 Suppl. 1:282-91
38. Tyler-Cross, R., et. Protein Science. 3: 620-627
39. U.S. Pat. No. 5,874,500
40. U.S. Pat. No. 6,331,422
41. US 2003/0166833
42. US 2003/0187232
43. U.S. Pat. No. 4,672,032 (Slavkin)
44. Williams, et al., Journal of Comparative Neurobiology, 264:284-290 (1987).
45. Williams, Neurochemical Research, 12:851-869, 1987
46. WO 00/44808
47. WO 00/53196
48. WO 01/97834
49. WO 02/080994
50. Zucker and Katz, (1991). Exper. Biol. Med.: 693-702

The invention claimed is:

1. A pharmaceutical and/or therapeutic formulation for promoting regeneration of tooth supporting tissues, and/or bone tissue, comprising a polymeric matrix and an active enamel substance comprising at least 90% amelogenin and/or a biologically active fragment thereof, wherein the concentration of said amelogenin and/or a biologically active fragment thereof is less than 250 µg/ml of formulation.

2. A pharmaceutical and/or therapeutic formulation according to claim 1 for inducing osteogenesis.

3. A pharmaceutical and/or therapeutic formulation according to claim 1, wherein the concentration of amelogenin and/or a biologically active fragment thereof, is less than 100 µg/ml.

4. A pharmaceutical and/or therapeutic formulation according to claim 1, wherein the concentration of amelogenin and/or a biologically active fragment thereof, is one of:
less than 50 µg/ml,
at most 25 µg/ml,
at most 20 µg/ml,
at most 10 µg/ml,
at most 5 µg/ml, or
at most 1 µg/ml.

5. A pharmaceutical and/or therapeutic formulation according to claim 1, wherein the concentration of amelogenin and/or a biologically active fragment thereof is between 1 µg/ml and less than 250 µg/ml.

6. A pharmaceutical and/or therapeutic formulation according to claim 1, wherein said polymeric matrix comprises polyethyleneglycol.

7. A pharmaceutical and/or therapeutic formulation according to claim 1, wherein said matrix is suitable for cellular in growth or migration.

8. A pharmaceutical and/or therapeutic formulation according to claim 1, wherein said matrix is cell-occlusive.

9. A pharmaceutical and/or therapeutic formulation according to claim 1, wherein said matrix is preformed.

10. A pharmaceutical and/or therapeutic formulation according to claim 1, wherein said matrix is formed in situ.

* * * * *

UNITED STATES PATENT AND TRADEMARK OFFICE
CERTIFICATE OF CORRECTION

| | | |
|---|---|---|
| PATENT NO. | : 8,029,769 B2 | Page 1 of 1 |
| APPLICATION NO. | : 12/210350 | |
| DATED | : October 4, 2011 | |
| INVENTOR(S) | : Lyngstadaas et al. | |

It is certified that error appears in the above-identified patent and that said Letters Patent is hereby corrected as shown below:

Title Page

Please amend line (63) of Related U.S. Application Data as follows:

-- Continuation of Application No. 11/721,192 filed on October 24, 2007, a national stage of PCT Application No. PCT/IB2005/004134 filed December 12, 2005--

In col. 48, line 28:

"in growth" should be --in-growth--

Signed and Sealed this
Fifteenth Day of November, 2011

David J. Kappos
*Director of the United States Patent and Trademark Office*